US009109206B2

(12) United States Patent
Sabaawy

(10) Patent No.: US 9,109,206 B2
(45) Date of Patent: Aug. 18, 2015

(54) METHOD FOR TREATING CHRONIC NERVE TISSUE INJURY USING A CELL THERAPY STRATEGY

(75) Inventor: Hatem Sabaawy, Neshanic Station, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 13/502,147

(22) PCT Filed: Oct. 16, 2009

(86) PCT No.: PCT/US2009/061093
§ 371 (c)(1),
(2), (4) Date: May 16, 2012

(87) PCT Pub. No.: WO2011/046570
PCT Pub. Date: Apr. 21, 2011

(65) Prior Publication Data
US 2012/0276068 A1 Nov. 1, 2012

(51) Int. Cl.
A61P 25/00 (2006.01)
A61K 35/28 (2006.01)
C12N 5/0775 (2010.01)
A61K 35/12 (2015.01)

(52) U.S. Cl.
CPC ......... C12N 5/0663 (2013.01); A61K 2035/124 (2013.01)

(58) Field of Classification Search
None
See application file for complete search history.

(56) References Cited

U.S. PATENT DOCUMENTS

2006/0233766 A1 10/2006 Messina et al.

FOREIGN PATENT DOCUMENTS

WO 0178753 A2 10/2001

OTHER PUBLICATIONS

Silani, Vincenzo; et al; "Stem-cell therapy for amyotrophic lateral sclerosis" The Lancet, 364, 200-202, 2004.*
Zhao, Li-Ru; et al; "Human Bone Marrow Stem Cells Exhibit Neural Phenotypes and Ameliorate Neurological Deficits after Grafting into the Ischemic Brain of Rats" Experimental Neurology, 174, 11-20, 2002.*
Qian, Lichuan; Saltzman, W. Mark; "Improving the expansion and neuronal differentiation of mesenchymal stem cells through culture surface modification" Biomaterials, 25, 1331-1337, 2004.*
Neuhuber, Birgit; et al;"Axon growth and recovery of function supported by human bone marrow stromal cells in the injured spinal cord exhibit donor variations" Brain Research, 1035, 73-85, 2005.*
Saito, Fukuki; et al; "Spinal cord injury treatment with intrathecal autologous bone marrow stromal cell transplantation: the first clinical trial case report: The First Clinical Trial" The Journal of Trauma Injury, Injury, Infection and Critical Care, 64, 53-59, 2008.*
Pittenger, M.F. Mutlilineage Potential of Adult Human Mesenchymal Stem Cells. Science 284, 143-7 (1999).

(Continued)

Primary Examiner — Blaine Lankford
Assistant Examiner — David Berke-Schlessel
(74) Attorney, Agent, or Firm — Fox Rothschild LLP

(57) ABSTRACT

A method for treating a degenerative or traumatic injury to a nerve tissue or the brain by administering at or near the injury site a composition containing adherent bone marrow stem cells suspended in a pharmaceutically acceptable liquid in an amount effective to elicit axonal regeneration or re-myelination at the site of injury.

9 Claims, 13 Drawing Sheets

(56) References Cited

OTHER PUBLICATIONS

Arnhold, S. et al. Human Bone Marrow Sroma Cells Display Certain Neural Characteristics and Integrate in the Subventricular Compartment After Injection into the Liquor System. Eur. J. Cell. Biol. 85, 551-65 (2006).

Young, W. et al. Effect of High-dose Corticosteroid Therapy on Blood Flow, Evoked Potentials, and Extracellular Calcium in Experimental Spinal Injury. J. Neurosurg. 57, 667-73 (1982).

Grove, et al. "Plasticity of bone marrow-derived stem cells." Stem Cells 22: 487-500. (2004).

Gray, et al. "Sciatic Nerve Block in a Child: A Sonographic Approach." Anesth. Analg. 97: 1300-1302. (2003).

Darwin J Prockop, "Repair of Tissues by Adult Stem/Progenitor Cells (MSCs): Controversies, Myths, and Changing Paradigms", Molecular Therapy vol. 17 No. 6, 939-946 Jun. 2009.

Adam P. Croft et al., "Formation of Neurons by Non-Neural Adult Stem Cells: Potential Mechanism Implicates an Artifact of Growth in Culture", StemCells 2006;24:1841-1851.

Akira Igarashi et al., "Selection of Common Markers for Bone Marrow Stromal Cells from Various Bones Using Real-Time RT-PCR: Effects of Passage Number and Donor Age", Tissue Engineering vol. 13, No. 10, 2007, pp. 2405-2417.

Neuhuber, B. et al., "Axon growth and recovery of function supported by human bone marrow stromal cells in the injusred spinal cord exhibir donor vairiations," Brain Research, 2005 vol. 1035, pp. 73-85.

Qian, L. et al., "Improving the expansion and neuronal differentiation of mesenchymal stem cells through culture surface modification," Biomaterials, 2004, vol. 25, pp. 1331-1337.

Shi et al., "Therapeutic Benefit of Intrathecal Injection of Marrow Stromal Cells on Ischemia-Injured Spinal Cord." Ann. Thorac. Surg. 83: 1484-1490. (2007).

Wright et al., "The cell culture expansion of bone marrow stromal cells from humans with spinal cord injury: implications for future cell transplantation therapy." Spinal Cord 46: 811-817. (2008).

\* cited by examiner

METHOD FOR TREATING CHRONIC NERVE TISSUE INJURY USING A CELL THERAPY STRATEGY

The present application is the U.S. National Phase of International Patent Application Serial No. PCT/US09/61093, filed Oct. 16, 2009, the contents of which are hereby incorporated by reference.

FIELD OF THE INVENTION

The present invention relates to cells, compositions, and methods of cell therapy by administering to an affected subject a therapeutically effective amount of a population of adhesive bone marrow cells to treat a traumatic or degenerative nerve or brain injury.

BACKGROUND OF THE INVENTION

Nerve and brain injuries, including traumatic and degenerative injuries to peripheral nerves and/or the spinal cord (SCI), still remain with no curative therapy. With respect to SCI for example, even a mild contusion to the spinal cord can result in massive neuronal and glial cell loss, demyelination, cavitation, and glial scarring. Pathological changes such as these have detrimental functional effects causing loss of sensory perception, distal motor paralysis, and severe functional impairment, with the final outcome depending upon axonal sparing, remyelination, and possibly neural regeneration. Similar effects are also observed with many neurodegenerative disorders including, inter alia, Alzheimer's Disease, Parkinson's Disease, Multiple Sclerosis, Amyotriphic Lateral Sclerosis, multiple-system degenerations, cerebellar degeneration, and the like. Accordingly, one or more strategies are desirable to repair or regenerate damaged tissue with the ultimate outcome of restoring such tissue and lost functional effects.

One proposed strategy is the use of pluripotent cells or stems cells for the purposes of treating the affected area. Marrow stromal cells, in particular, are attractive candidates for such purposes because they have many of the characteristics of stem cells and have been shown to differentiate into osteoblasts, chondrocytes, adipocytes, and even myoblasts. Thus, there is potential for their use in regenerating damaged nervous or brain tissue in a patient.

One of the primary difficulties is that marrow cell types are relatively rare and difficult to identify. To this end, much of the current research has been centered around isolating particular cell types of interest and exploring methodologies for achieving neural cell differentiation. U.S. Patent Application Publication No. 2007/0031387, for example, discloses the isolation of mononuclear cells from granulocytes within a population of bone marrow cells. U.S. Pat. No. 7,098,027 alternatively isolates mononuclear cell isolation using density-gradient centrifugation, i.e. by isolating cells having a specific gravity within the range of 1.07 and 1.08 g/ml. In either of the two cases, the isolated mononuclear cells are contemplated for administration for treatment of spinal injury or other neurological disorders.

Beyond cell isolation, there have been numerous attempts to differentiate BM cells either before administration in an in vitro environment or after administration in vivo. U.S. Pat. No. 5,197,985, for example, illustrates methods for regenerating mesenchymal and neuroectodermal tissues using adult bone marrow (BM) cells. Cell differentiation is accomplished using a porous ceramic composition of tri-calcium phosphate or hydroxyapatite or combinations of the two, as a vehicle or carrier for marrow-derived mesenchymal cells, which, when implanted into skeletal defects, promotes the differentiation of the cells into skeletal tissue.

U.S. Pat. No. 6,528,245 discloses a method of specifically selecting for bone marrow stromal cells in a bone marrow cell population by incubating the cells in a plastic culture medium and removing the stromal cells that adhere to the plastic. These cells are then differentiated in vitro in the presence of retinoic acid, growth factors, and fetal neuronal cells and are administered for treating neurodegenerative disorders. U.S. Patent Application Publication No. 2006/0275272 similarly teaches treatment methods by isolating and culturing bone marrow stromal cells to be used for such purposes. Finally, U.S. Pat. No. 7,279,331, teaches similar methods of isolating bone marrow stromal cells, which are then pre-differentiated in vitro into a neuronal cell using antioxidants and/or various growth factors.

U.S. Patent Application Publication No. 2006/0029580 further teaches a method of generating neural progenitor cells by incubating bone marrow cells in a culture supplemented with fibroblast growth factor-2 (FGF-2) and epidermal growth factor (EGF). The progenitor cells may then be administered to a patient exhibiting a neuropathologic condition.

Beyond BM cells, cells derived from placental or other post-natal tissue have also been explored for neural regenerative purposes. U.S. Patent Application Publication No. 2006/0147426 relates to cell culture conditions for isolating postnatal, multilineage inducible cells. Such culture conditions include extracellular matrix substrate, oxygen tension, growth factors and vitamins, cell density, or co-culture of cells. U.S. Patent Application Publication No. 2005/0032209 teaches methods and compositions for regenerating or repairing neural tissue using postpartum-derived cells. These cells are derived from placental or umbilical cord tissue and are grown on L-valine media in a 5% oxygen environment.

The foregoing presents definitive evidence that bone marrow and similar pluripotent cell types can differentiate into mesenchymal cells, and further illustrates the feasibility and promise of applying these cell types for treatment of traumatic or degenerative injury to nerve or brain tissue, such as remyelination or regeneration of damaged axonal tissue. Even in view of the proposed methodologies above, however, there remains a need for alternative cell populations and novel strategies for more predicable cell differentiation. In addition, there is a need to circumvent the numerous ethical and technical constraints that now limit the widespread use of neural transplant.

The instant invention through its embodiments and examples addresses these needs.

SUMMARY OF THE INVENTION

The present invention relates to cells, compositions, and methods of cell therapy comprising administering to an affected subject a therapeutically effective amount of isolated adhesive bone marrow cells from a bone marrow cell population to treat a traumatic or degenerative nerve or brain injury. As provided herein, the present invention is based on the discovery that adherent bone marrow cells (ABMC) can differentiate into and/or elicit the production of neural progenitor cell types, myelin forming cells, astrocytes, oligodendrocytes, mature neurons, myelinated axons and the like. More specifically, it was surprisingly discovered that when isolated ABMCs are introduced into a lesion of a mammal suffering from a nerve injury, such as SCI, the cells lead to both remyelination and axonal regeneration of damaged neural tissue at the lesion site. Improved motor coordination and/or a reduction of the targeted neurodegenerative condition were also observed, particularly when combined with physical therapy.

Therefore, according to one aspect of the present invention, a method for treating a degenerative or traumatic injury to a nerve tissue or the brain is provided, by which there is administered at or near the injury site a composition containing adherent bone marrow stem cells suspended in a pharmaceutically acceptable liquid in an amount effective to elicit axonal regeneration or re-myelination at the site of injury. According to one embodiment of this aspect of the invention, the injury is to the brain or spinal cord and bone marrow stem cells are administered by intrathecal injection through lumbar puncture into the cerebrospinal fluid at or near the injury site. According to another embodiment of this aspect of the invention, the injury is to a peripheral nerve and the bone marrow stem cells are administered by sonography guided local delivery to the root of the peripheral nerve.

In another embodiment of the invention, the adherent bone marrow stem cells elicit both axonal regeneration and re-myelination at the site of the injury. In another embodiment of the invention, the bone marrow stem cells are derived from umbilical cord blood or bone marrow aspirates.

A therapeutically effective amount of cells are administered to the patient to treat the nerve or brain injury. In one embodiment, a therapeutically effective amount refers to the amount of cells necessary to elicit remyelination and/or axonal regeneration of damaged neural tissue at a lesion site or otherwise to repair damaged nerve or brain tissue. This, in turn, can facilitate improved motor coordination and/or a reduction of the targeted neurodegenerative condition A therapeutically effective dosage is between about $10^4$ to about $10^7$ ABMCs/kg. As exemplified below, in one non-limiting embodiment, a therapeutically effective dosage is approximately $2 \times 10^6$ ABMCs/kg.

Such a therapeutically effective dosage may be provided to the patient as single administration or multiple cumulative administrations and may also include one or more pharmaceutically acceptable additives so long as it does not affect adversely the action or differentiation of ABMCs. In one embodiment, the cumulative dosage of said bone marrow stem cells is administered periodically over a series of two or more injection. In a more specific embodiment, the periodic injections are performed monthly.

The isolated subpopulation of ABMCs are positive for one or more cluster of differentiation (CD) cell surface markers indicative of the multilineage differentiation potential, particularly neural differentiation. In one embodiment of the invention, the bone marrow stem cells include cells positive for one or more markers selected from CD44, CD73, CD90, CD105, CD166 and CD271. According to a more specific embodiment, the bone marrow stem cells are negative for the markers CD34, CD38 and CD45. The presence (or absence) of these markers may be confirmed using one or more procedures discussed herein or otherwise known in the art.

In another embodiment, which is exemplified below, ABMCs include or result in the production of one or more myelin forming cells, astrocyte precursor cells, astrocytes, neural progenitor cells, oligodendrocyte precursor cells, oligodendrocyte cells, myelinated axons, mature neurons, and the like. To this end, newly formed cells were found to be positive for one or more markers associated with these cells types such as, but not limited to, NF70, Nestin, PDGFR, GFAP, or TuJ1.

In the present invention, biological samples containing bone marrow stem cells are first obtained using standard methods known in the art and as discussed herein, for example, from umbilical cord blood or bone marrow aspirates. A sub-population of ABMCs is then isolated for use in the inventive method.

Therefore, according to another aspect of the present invention, a method for treating a degenerative or traumatic injury to a nerve tissue or the brain in a vertebrate is provided including the steps:

(a) culturing a biological sample containing adult bone marrow stem cells on a poly-L-lysine coated substrate, so that a layer of bone marrow stem cells adheres to the substrate;

(b) washing any non-adherent cells from the substrate and collecting the bone marrow stem cell layer;

(c) suspending the adherent bone marrow stem cells in a pharmaceutically acceptable liquid; and (d) administering near the injury site the bone marrow stem cell suspension in an amount effective to elicit axonal regeneration or remyelination at the site of injury.

In one embodiment the culturing step is performed for between 2 and 72 hours, and in a further embodiment, the amount of time is approximately 72 hours. In another embodiment, after incubation, non-adherent cells are removed by flushing the coated substrate using one or multiple washing steps. Adherent cells are then detached from the poly-L-lysine coated substrate.

ABMCs are then administered to the patient at or approximately at the site of injury/damage using any mode of administration understood in the art. In one non-limiting embodiment, the ABMCs may be formulated for direct injection, at or near the site of injury. To this end, the cells may be suspended in a sterile solution, which may include one or more of a physiological saline, distilled water, spinal fluid or other pharmaceutically acceptable liquids. For the treatment of spinal cord injury, administration is by intrathecal injection, Alternative embodiments for modes of administration are further provided herein, or are otherwise understood by one of ordinary skill in the art.

The ABMCs and compositions of the instant invention are advantageous in contributing to axonal regeneration and remyelination at a spinal cord or peripheral nerve lesion. They are further advantageous to otherwise repair damaged/injured nerve or brain tissue. With respect to patients having spinal cord injury, i.e. motor paralysis or sensory loss, ABMC transplantation is effective to promote axonal regeneration and remyelination and induce repair, particularly when combined with functional training by physiotherapy. Regeneration of corticospinal tract fibers was also observed and was matched by functional improvement. Also, the ABMCs produced neurotrophic factors and anti-inflammatory mediators that supported the host nerve tissue by creating new neuronal pathways in the fibrous scar tissues, or by expanding sprouting or generating short regenerated neuronal fibers.

Additional advantages of the instant invention will be appreciated by a skill artisan based upon the teachings and exemplifications provided herein.

DETAILED DESCRIPTION OF THE INVENTION

Figure 1:
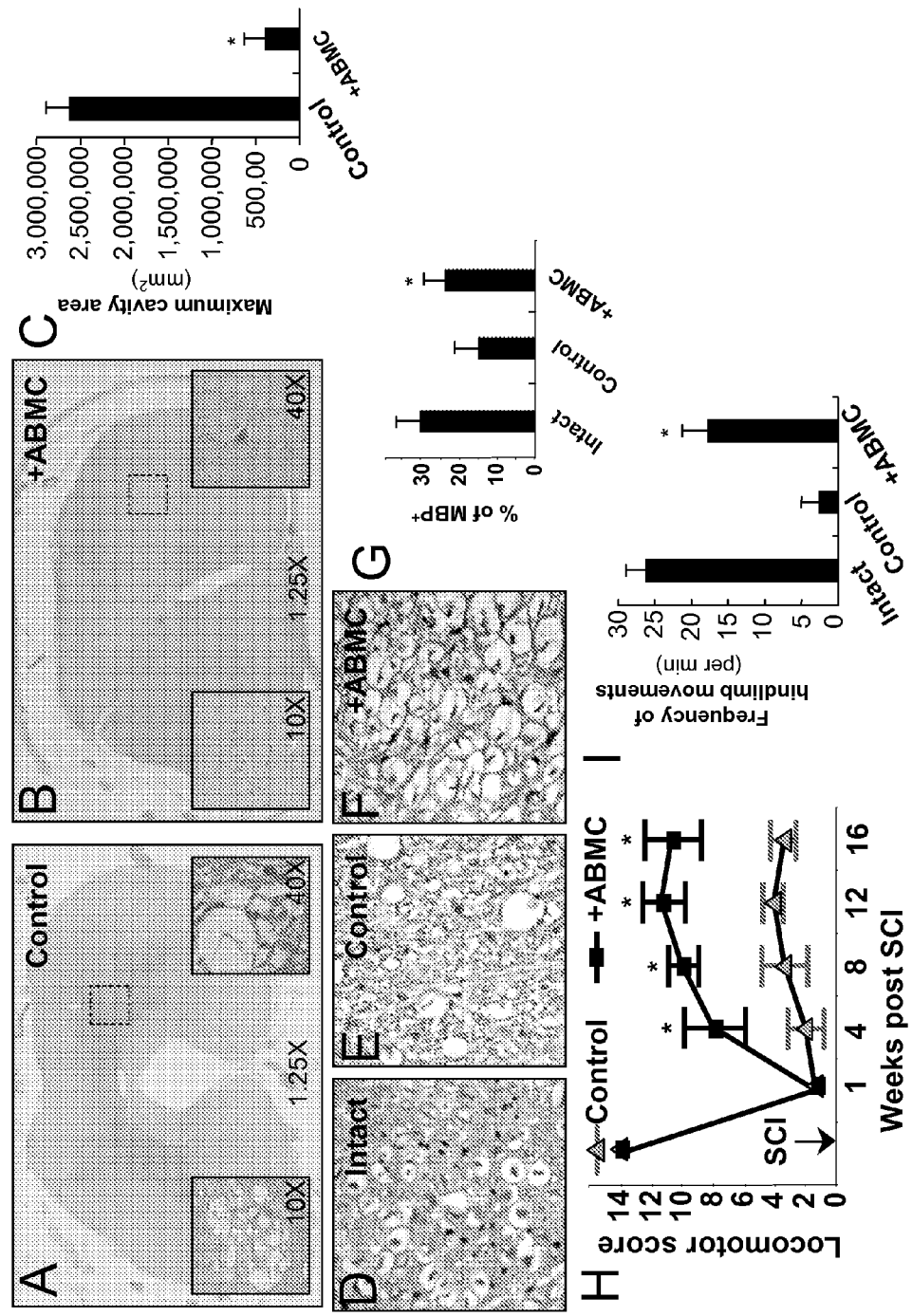
FIG. 1 illustrates histopathological findings at 16 weeks post ABMC cell therapy in the canine severe SCI model. (A) The epicenter of injured canine spinal cord in the control group stained with H&E, showed marked vacuolation (Inert), and glial scarring. (B) The epicenter of injured spinal cord of a dog in group B treated with autologous ABMC, revealing remyelination and less cavitation. (C) Quantitative analysis of cavity areas showing significant decrease in cavities in dogs treated with autologous ABMC. (D-F) Myelin basic protein immunostaining of intact spinal cord in uninjured dog (D), control SCI dog (E), and dog treated with autologous ABMC (F). (G) Recovery of myelin basic protein staining to near normal levels in intact dogs after treatment with autologous ABMC. (H) Locomotor scores of dogs at baseline, and one, 4, 8, 12, and 16 weeks after SCI demonstrating significant improvement in dogs treated with autologous ABMC as early as 4 weeks post transplantation. (I) Increase in hindlimb movements in dogs treated with autologous ABMC compared to controls.

The present invention relates to cells, compositions, and methods of cell therapy comprising administering to an affected subject a therapeutically effective amount of isolated adhesive bone marrow cells from a bone marrow cell population to treat a traumatic or degenerative nerve or brain injury. As provided herein, the present invention is based on the discovery that adherent bone marrow cells (ABMC) differentiate into or elicit the production of neural progenitor cell types, myelin forming cells, astrocytes, oligodendrocytes, mature neurons, myelinated axons and the like. More specifically, it was surprisingly discovered that when isolated ABMCs are introduced into a mammal suffering from a nerve injury, e.g. SCI, the net effect is remyelination and axonal regeneration of damaged neural tissue at the lesion site. This was observed to further lead to improved motor coordination and/or a reduction of the targeted neurodegenerative condition, particularly when combined with physical therapy.

Bone marrow cell populations of the present invention may be obtained using any method known in the art. In one embodiment, the bone marrow population of cells may be aspirated by removing bone marrow fluid and cells through a needle inserted into the bone. Bone marrow aspiration may be performed on the iliac crest, but is not limited to this site and may be performed at any other site of the body known for aspirating or otherwise obtaining bone marrow cells. In certain embodiments, the bone marrow cells are autologously obtained from the affected patient. The present invention, however, is not so limiting and the bone marrow cell population also may be obtained from any other source known in the art, such as but not limited to a bone marrow bank (or similar sources or bone marrow derived from a non-relative of the patient), bone marrow from a relative, or marrow from any other non-fetal animal source, cord blood, adipose tissue, biological fluids, or any other source known in the art, which is immunologically compatible with the patient.

Regardless of its source, bone marrow cells are isolated from the aspirate using standard methods known in the art. In one non-limiting embodiment, the bone marrow aspirate is diluted with a buffering formulation, e.g. RPMI-1640, and centrifuged in the presence of a cell separating medium, such as Ficoll-Plaque Plus™ (Amersham Biosciences). The supernatant is removed, and the pelleted cells resuspended and maintained using standard medium for pluripotent cell maintenance. In a non-limiting example, such medium may include DMEM containing low glucose amounts and supplemented with FBS, L-glutamine, at least one broad spectrum antibiotic and $CO_2$. Other medium types may also be used as otherwise known in the art.

From this population of bone marrow cells, a subpopulation of ABMCs are then isolated. In one non-limiting embodiment, ABMCs are isolated by culturing the cells on a poly-L-lysine coated substrate without expanding the cells in culture. To this end, cells may be suspended on a poly-L-lysine coated dish, flask, bag, or other similar material know in the art for culturing pluripotent cells. In one non-limiting embodiment, the cells are suspended at a density of approximately $2.0 \times 10^5$ cells/cm$^2$. The coating substrate may be further comprised of any standard medium for marrow cell survival that is known in the art, e.g. α-MEM containing L-glutamine, one or more broad spectrum antibiotics and FBS, or the like.

The bone marrow cell population is incubated on the a poly-L-lysine coated substrate for an effective amount of time to distinguish adherent bone marrow cells from non-adherent bone marrow cells. In one embodiment such an effective amount of time is between 2 and 72 hours. In further embodiments, the effective amount of time is approximately 72 hours.

After incubation, non-adherent cells are removed by flushing the coated substrate using one or multiple washing steps. Any flushing agent known in the art may be utilized for the washing steps and may include, but is not limited to, saline, PBS, FBS, dH$_2$O, medium, or similar flushing agents that are known in the art. In certain embodiments, the cells are flushed three times to remove non-adherent cells.

After flushing, adherent cells are detached from the poly-L-lysine substrate using methods known in the art. For example, in one embodiment the isolated ABMCs are detached from the poly-L-lysine coated substrate by incubating the substrate in the presence of Accutase. In certain embodiments, cells are lifted by incubation with Accutase at 37° C. for 5 min. However, the present invention is not so limited and similar methods of lifting adherent cells or methods otherwise understood in the art are also contemplated.

In further embodiments, the subpopulation of AMBCs also may be isolated using one or more of the methods disclosed in U.S. Provisional Application No. 61/252,389, filed Oct. 16, 2009, the contents of which are incorporated herein by reference.

Cells within the isolated subpopulation of ABMCs are positive for one or more cluster of differentiation (CD) cell surface markers that are indicative of the multilineage differentiation potential, particularly neural differentiation. Such markers may be comprised of, but are not limited to, one or more of the following CD44, CD73, CD90, CD105, CD166, and CD271. In certain embodiments, the AMBCs of the instant invention may exhibit no expression of CD14, CD34, CD38, and CD45. The presence or absence of these CD cell surface markers may be identified using one or more procedures known in the art. In one embodiment, such a procedure includes flow cytometry after the 2-72 hour incubation. General immunoassays known in the art for cell surface marker identification may also be employed and are well known to those skilled in the art. To this end, both polyclonal and monoclonal antibodies can be used in the assays. Where appropriate other immunoassays, such as enzyme-linked immunosorbent assays (ELISAs) and radioimmunoassays (RIA), can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al., *Molecular Cloning: A Laboratory Manual*, Cold Springs Harbor, N.Y. (1989).

Prior to administration, it is preferred that the ABMCs are minimally manipulated from the originally isolated form in that their exposure to environmental conditions and/or media that would elicit differentiation is minimized or entirely avoided. In the alternative, however, the present invention is not necessarily limited as such. In certain embodiments, the entirety of or a subset of ABMCs may be predifferentiated into a neural lineage. In a non-limiting example, the entirety of or a subset of ABMCs may be incubated on a neuronal induction medium commonly known in the art for approximately 1-3 days immediately prior to administration. Such medium may include, but is not limited to, DMEM/F12 with 2% DMSO and 1 mM forskolin.

The ABMCs of the instant invention may be administered to the patient at or approximately at the site of injury/damage. The mode of administration of the cells may vary depending on several factors including the type of injury/disease being treated, the age of the mammal, whether the cells are differentiated, whether the cells have heterologous DNA introduced therein, and the like. An example of administration of the cells at the spinal tissue is provided herein in the experimental Examples section. In that example, cells are introduced at the cerebrospinal fluid of the mammal intrathecally near the site of a spinal cord injury. To this end, cells may be introduced to the desired site by direct injection, such as an intrathecal injection, through lumbar puncture into the cerebrospinal fluid of the patient at or near the injury site.

The instant invention is not necessarily limited to intrathecal injection or such a methodology, however. In alternative embodiments, where the nerve injury is to a peripheral nerve, such as the injury to the median nerve associated with carpal tunnel syndrome, the cells may be administered by sonography guided local delivery to the root of the peripheral nerve. The cells can also be administered to a site near or within the same bodily region of the injury and allowed to infuse to the site of injury using one or more methods known in the art. For example, with respect to administration to a site in the brain, cells can be administered intrathecally, or otherwise using one or more of the methods herein, and allowed to infuse to the damaged tissue of the brain.

Where necessary, the cells may be equipped with one or more appended groups, e.g. peptides or other biological agents, facilitating transport across the blood-brain barrier. Again, the foregoing methods are not limiting to the invention and cells can be administered into a host by any method as long as cells can be infused safely and certainly, such as, but not limited to, intravascularly, intracerebrally, parenterally, intraperitoneally, intravenously, epidurally, intra-spinally, intrasternally, intra-articularly, intra-synovially, intracerebrally, intra-arterially, intra-cardiacly, or intramuscularly. Transplantation of the cells of the present invention using any of the forgoing modes, or other similar modes known in the art, also can be accomplished using techniques provided herein or otherwise known in the art.

ABMCs are generally used for transplantation as a composition in the form of suspension in physiological saline, distilled water, spinal fluid or the like. In one embodiment, for example, the composition is comprised of ABMCs suspended in approximately 150 µl of saline. Again, the present invention is not necessarily limited to this composition and ABMCs can also be formulated into a composition suitable for administration as a suspension in an appropriate buffer such as PBS or otherwise within a pharmaceutically acceptable liquid. The ABMCs also may be cryopreserved in physiological saline, and reconstituted by suspending into a solvent above before use. The method of isolation and preservation of ABMCs, and preparation of a composition are known to a skilled person in the art pertaining to cell transplantation. Such a composition of ABMCs is useful when it is difficult to obtain ABMCs autologously from the patient.

As noted herein, a therapeutically effective amount of cells are administered to the patient to treat the traumatic or degenerative nerve or brain injury. In one embodiment, a therapeutically effective amount refers to the amount of cells necessary to elicit remyelination and/or axonal regeneration of damaged neural tissue at a lesion site or otherwise repair damaged nerve or brain tissue. This, in turn, can facilitate improved motor coordination and/or a reduction of the targeted neurodegenerative condition. In one non-limiting embodiment, between about $10^4$ to $10^7$ AMBCs/kg of the subject are administered to the patient as a therapeutically effective amount. In a further embodiment, and as exemplified in the Examples below, a therapeutically effect dosage may be approximately $2 \times 10^6$ ABMCs/kg of the subject.

The ABMC containing composition of the present invention may be administered to a patient with a nerve or brain injury as early as possible after injury. However, as illustrated in the Examples below, one of ordinary skill in the art will understand that the timing of treatment or the like is generally determined by a physician and is not necessarily limiting to the instant invention. To this end, a patient may be treated at later stage depending on her/his conditions and other factors.

A therapeutically effective dosage may be provided to the patient as single administration or multiple administrations. In the case of the latter, the therapeutically effective amount may be divided between multiple administrations, such as between 2 and 8 separate administrations. Such administration may occur successively over a multi-day period or as discrete administrations received daily, weekly, monthly, etc. Again, a skilled artisan will understand that the timing of treatment and/or number of administrations may be generally determined by a physician and is not necessarily limiting to the instant invention.

The composition of ABMCs may also contain any pharmaceutically acceptable additive so long as it does not affect adversely the action or differentiation of ABMCs. For example, when a patient is treated with ABMCs harvested from an exogenous source, one or more known immunosuppressants may be preliminarily administered. Immunosuppressants can be selected from those generally used in the bone marrow- or organ-transplantation, such as but not limited to cyclosporin, tacrolimus hydrate (FK506), cyclophosamide, azathioprine, mizoribine and methotrexate. The dosage of immunosuppressant can be determined appropriately considering the kinds of the drug, origin of ABMCs to be administered, tolerance of the patient, and the like.

The instant invention is advantageous in contributing to axonal regeneration and re-myelination at a spinal cord lesion site, or repair of other nerve or brain damaged sites (e.g. peripheral nerve damage, brain damage, etc.). With respect to patients having spinal cord injury, i.e. motor paralysis or sensory loss, ABMC transplantation, particularly when combined with functional training by physiotherapy, are effective promoters of axonal regeneration and re-myelination, and induce repair after SCI. As exemplified below, ABMCs include or result in the production of one or more myelin forming cells, astrocyte precursor cells, astrocytes, neural pro-genitor cells, oligodendrocyte precursor cells, oligodendrocyte cells, myelinated axons, mature neurons, and the like. To this end, newly formed cells were found to be positive for one or more markers associated with these cells types such as, but not limited to, NF70, Nestin, PDGFR, GFAP, or TuJ1. Regeneration of corticospinal tract fibers was also observed and was matched by functional improvement.

Without intending to be bound by theory, it is surmised that axonal regeneration likely plays a major role, either directly or through recruitment of neural progenitor cells from the brain neural crest that mature into Schwann cells or spinal cord tissue stem cells in the ependymal region around the central canal. In the exemplifications below, this region was where largest number of ABMC derived cells were found, along with colacolized spinal cord resident progenitor markers. ABMC also produce neurotrophic factors and anti-inflammatory mediators that support the host spinal cord tissue by creating new neuronal pathways in the fibrous scar tissues, or by expanding sprouting or generating short regenerated neuronal fibers. Moreover, ABMC may provide guidance for connection to the distal and proximal ends of the nerve tissue, and facilitate regeneration of the transplanted cells.

Spinal cord and peripheral nerve injury and brain injury are not necessarily limited to physical injury and may also be associated with a disease state. Accordingly, use of ABMCs may also be contemplated for use in the treatment of neurodegenerative disease states. For example, among neonates and children, the cells may be used for treatment of a number of genetic diseases, including, but not limited to, Tay-Sachs disease and the related Sandhoff's disease, Hurler's syndrome and related mucopolysaccharidoses and Krabbe's disease. With respect to adult diseases of the CNS, the cells of the present invention are useful for treatment of Parkinson's disease, Alzheimer's disease, amyotropic lateral sclerosis, Huntington's disease, epilepsy and the like. Other neurodegenerative diseases include but are not limited to, AIDS dementia complex; demyelinating diseases, such as multiple sclerosis and acute transferase myelitis; extrapyramidal and cerebellar disorders, such as lesions of the ecorticospinal system; disorders of the basal ganglia or cerebellar disorders; hyperkinetic movement disorders, such as Huntington's Chorea and senile chorea; hypokinetic movement disorders; progressive supranucleopalsy; structural lesions of the cerebellum; spinocerebellar degenerations, such as spinal ataxia, Frie-dreich's ataxia, cerebellar cortical degenerations, multiple systems degenerations (Mencel, Dejerine Thomas, Shi-Drager, and Machado-Joseph), systermioc disorders, such as Rufsum's disease, abetalipoprotemia, ataxia, telangiectasia; and mitochondrial multi-system disorder; and disorders of the motor unit, such as neurogenic muscular atrophies; Down's Syndrome in middle age; Diffuse Lewy body disease; Senile Demetia of Lewy body type; Wernicke-Korsakoff syndrome; Creutzfeldt-Jakob disease; Subacute sclerosing panencephalitis hallerrorden-Spatz disease; and Dementia pugilistica. See, e.g., Berkow et. al., (eds.) (1987), The Merck Manual, (15th edition), Merck and Co., Rahway, N.J., which reference, and references cited therein, are entirely incorporated herein by reference.

The following non-limiting examples set forth hereinbelow illustrate certain aspects of the invention.

EXAMPLES

Materials and Methods

Isolation and Culture of Canine Adherent BM Cells (cABMC)

All aspects of animal care and treatment were carried out according to NIH guidelines and the guidelines of the animal care committee. ABMC were isolated from the femurs of adult dogs. Briefly, the low-density mononuclear cells were isolated using Ficoll-Plaque Plus (Amersham Biosciences), and maintained in Dulbecco's modified Eagle's medium (DMEM)-low glucose supplemented with 10% fetal bovine serum (FBS), with 2 mg/ml L-glutamine (Gibco) and 0.3% penicillin streptomycin (Gibco) at 37° C. and 5% CO2 concentration. ABMC were subjected to flow cytometry to determine purity as described Pittenger, M. F. *Mutlilineage Potential of Adult Human Mesenchymal Stem Cells. Science* 284, 143-7 (1999). In vitro GFP labeling was done by adding pCMV-AcGFP plasmid mixed with lipofectamine at 2:1 ratio to each plate and incubated at 37° C. for 6 h before transplantation.

Isolation and Culture of Human ABMC (hABMC)

Human ABMC were isolated using bone marrow aspirates from the iliac crest of SCI patients. Samples were obtained after signing an informed consent. Cells were diluted 1:1 with RPMI-1640 and layered on top of 15 ml Ficoll-Plaque Plus in 50 ml tubes and centrifuged for 30 min at 800 g at room temperature. The cell interface was diluted to about 15 ml with media and centrifuged for 10 min at 400 g. After discarding the supernatant, the pellet was resuspended in 1 ml medium. The nucleated cells were counted, suspended at a density of $2 \times 10^5$ cells/cm$^2$ on poly-L lysine coated dishes in standard medium containing α-MEM supplemented with 2 mg/ml L-glut-amine, 1% antibiotic antimycotic, and 10% (v/v) non-heat-inactivated selected prescreened FBS.

The cells were incubated for 3 days, and non-adherent cells were removed by replacing the medium with three washing steps. The cells were lifted by incubation with Accutase at 37° C. for 5 min. For expansion to generate MSCs for comparison, and neural induction, ABMC were prepared as described above. Expanded cells were left to grow for 12-16 days before they were passaged and replated at a ratio of 1:4. Osteogenic, adipogenic, and chondrogenic differentiation were performed as described in Pittenger, M. F. et al. *Multilineage Potential of Adult Human Mesenchymal Stem Cells. Science* 284, 143-7 (1999). ABMC were analyzed by flow cytometry after staining with CD45-PC7, CD44-FITC, CD34-PE, CD73-PE, CD105-PE, CD106-PE, CD166-PE, and CD271-PE (all from BD Biosciences).

Neuronal Induction

Neuronal differentiation was performed as described in Arnhold, S. et al. *Human Bone Marrow Sroma Cells Display Certain Neural Characteristics and Integrate in the Subventricular Compartment After Injection into the Liquor System Eur. J. Cell. Biol.* 85, 551-65 (2006), with modification. Neurosphere induction was done by culture in serum free DMEM supplemented with 2% (v/v) B27 medium (Invitrogen) and the growth factors EGF (20 ng/ml, R&D systems), βFGF (20 ng/ml) and heparin (5 mg/ml)). Neural induction was done by using single cells prepared by Accutase and plated at a density of 2000 cells/cm$^2$ in serum-free DMEM/F12, with 2%

DMSO and 1 mM forskolin. Cells were kept under these conditions for four days and were then analyzed by immunofluorescence microscopy.

Canine Model of Severe Spinal Cord Injury

Sixteen healthy adult mongrel dogs that weighed 3.77±0.59 kg were used for the experimental spinal cord injury study. All aspects of animal care and treatment were carried out according to the guidelines of the animal care committee of Cairo University. Anesthetized (sodium pentobarbital, 40 mg/kg) dogs received severe spinal cord injury (SCI) at the L4 level as described in the cat model Young, W. et al. *Effect of High-dose Corticosteroid Therapy on Blood Flow, Evoked Potentials, and Extracellular Calcium in Experimental Spinal Injury. J. Neurosurg.* 57, 667-73 (1982), with modifications. Briefly, after L4 laminectomy, the dura was opened, and the spinal cord was transected. The severed ends of the cord typically retracted about 3 mm and were inspected under a surgical microscope to ensure complete transection. Postoperative care included that the dogs were kept warm, and given manual bladder evacuation twice per day and prophylactic antibiotics. The dogs had no difficulty in feeding.

The dogs were assigned, without bias, to four groups according to treatment after SCI. Transplantation of canine ABMC was performed one week after the SCI. The dogs were anesthetized using the same methods described above. The control group did not receive any cell transplant after the injury. In the three groups receiving unmanipulated ABMC, or ABMC induced for neural differentiation for 24 hours, or for 72 hours, cells suspended in 150 µl of saline solution were injected into the CSF by lumbar puncture. Behavioral assessment of the hind limb functional recovery was done by video recording. Each dog was videotaped from the sides and back for a minimum of 10 walking steps. Using a 15-point scoring system 25, the gait of each dog was scored from the videotapes by investigators blinded to treatment type, and the mean scores at baseline, one day after SCI, and at 4, 8, 12, and 16 weeks after the SCI were recorded.

Immunostaining

Cells were fixed in 4% paraformaldehyde and stored under PBS at 4° C. until stained. To assess the histopathological changes, all dogs were euthanized at 16 weeks after the cell therapy. Dogs were perfused with PBS and 4% paraformaldehyde, and spinal cords from T10 to L5 were fixed in 10% buffered neutral formalin, immersed in a decalcifying solution. Sections were embedded in paraffin and 4-1 µm thick axial sections were cut and stained with hematoxylin and eosin (H&E), or Luxol fast blue to identify myelin, or used for fluorescence analyses. Myelinated areas and volumes of the cavities from the epicenter of the damaged spinal cord were calculated from images of the transverse sections using Axio-Vision image analysis software (Zeiss). The section was identified with the largest area of cavitation, and this area was measured for each dog, and expressed as mean±SEM from control and cell therapy treated dogs. For immunofluorescence, the deparaffinized sections were processed through antigen retrieve for 2 min, and then stained with specific antibodies appropriate for canine cross-reactivity.

Primary antibodies were monoclonal anti-GFP, Clontech (1:100); polyclonal anti-GFAP, Dako (1:500); monoclonal anti-β-III tubulin, Chemicon (1:200); polyclonal anti-PDGFRα, Chemicon (1:80); monoclonal anti-GAD6, Abcam (1:500); polyclonal anti-Nestin, LifeSpan (1:100); monoclonal anti-acetylcholinestrase AE-1, Millipore (1:50); monoclonal anti-70 kDa Neurofilament, Milli-pore (1:50); monoclonal anti-A2B5, Millipore (1:100); and mono-clonal anti-GRM1, BD (1:100). Peroxidase ABC kit and $CoCl_2$-enhanced diaminobenzidine (DAB) were used as chromagen for myelin basic protein staining. For fluorescent microscopy, secondary antibodies labeled with Alexa Fluor 488, 535, and 610 dyes (Invitrogen) were employed. The targeted area chosen for calculating GFP, nestin, PDGFR, TuJ1, and NF70 counts using 100 squares with a surface area of 0.01 $mm^2$ each used for counting. Values are presented as mean±SEM. A pathologist who was blinded to the type of therapy performed all histological examinations.

Human Transplant

Eligible SCI patients were evaluated, and 159 patients were selected for initial screening. Eighty patients who met the inclusion criteria were enrolled (50 thoracic SCI, and 30 cervical SCI), and randomized into the two control and cell therapy groups, and both groups received scheduled standard physical therapy at the independent military forces center for physical medicine, rehabilitation and rheumatology. After formal admission to the trial, and signing a detailed informed consent, all participants in the transplant group underwent bone marrow aspiration under local anesthesia to produce ABMC. Aspirates were taken from the iliac region and placed immediately into a sterile container in cold culture medium and all subsequent processing was done as described above under complete clinical aseptic conditions at the stem cells center of Cairo University hospital. Patients received a cumulative target cell dose of 2×106 cells/kg, the ABMC cell numbers and viability were evaluated after the 72 hour adherence, and the procedure was repeated monthly until this target dose was achieved (Median was 4 injections, range was 1-8 injections).

Data and Statistical Analysis

All data were expressed as mean±SEM. Continuous data were compared by one-factor ANOVA followed by post hoc Fisher's protected least significant difference (PLSD) among all groups. For the quantitative analysis of the transplanted GFP cells in the spinal cord, fifteen cross sections were cut from each dog spinal cord at 4 µm thickness, 150 µm apart. All cells in each section with an average of 6 µM in diameter were counted. Three sections of spinal cord per antibody were examined for double-positive cells, and four regions per section were counted. Cavitation areas were compared between the control and cell therapy groups using Student t-test. For the functional testing, differences in locomotor scores between transplanted dogs and controls were analyzed at each time point using repeated measures ANOVA. Statistical significance was determined at the $P<0.05$ levels.

Example 1

In Vitro Differentiation of ABMC

Figure 5:
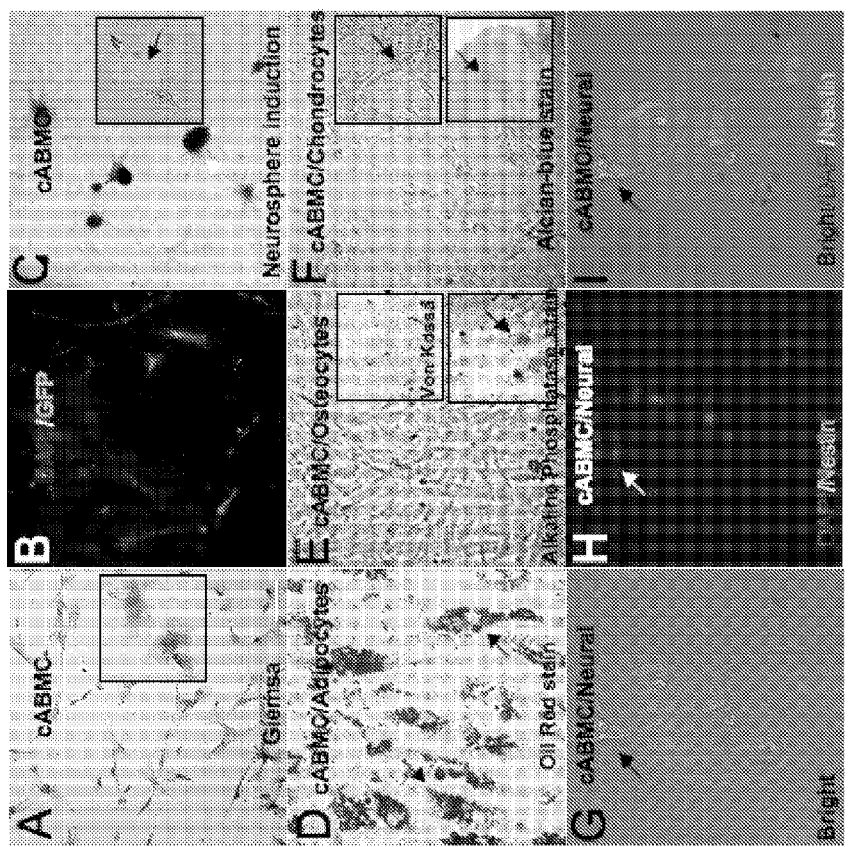
FIG. 5 illustrates canine ABMC tripotency and neural induction. (A) Canine adherent BM cells isolated after 72 hours (ABMC) and stained with giemsa. Inert show higher power image of the cells. (B) Canine ABMC transfected with GFP with '95% efficiency (All cells in this field are positive for GFP). (C) Neuronal induction of cABMC after one week showing neuronal morphology (upper inert) and neurosphere (lower inert). (D) cABMC induced for adipocytes and stained with oil red. (E) osteocyte differentiation with Von Kossa staining (upper inert) and alkaline phosphatase staining (lower inert). (F) Alician blue staining of cABMC induced for chondrocytes in either tissue culture plate (upper inert) or as chondroitin sulfate aggregates (arrow) in a tube 3D culture (lower inert). G-I Bright and GFP images of cABMC induced for neural differentiation and stained for Nestin.

Six canine BM samples were isolated and cultured for 72 hours on poly-L lysine under an approved protocol. Canine ABMC separated at 72 hours were found to express CD44, CD73, CD105, CD166, CD271, but had no or negligible expression of CD34, CD38, and CD45. Canine ABMC had a flat oblong morphology (FIG. 5A) with a limited number of fibroblast-like cells that predominate the traditional culture expanded MSC. Canine ABMC (FIG. 5A) were transfected with GFP expressing plasmid at near 90% efficiency (FIG. 5B). These cells retained their pluripotent potential and could be immediately and potently induced to adipocytes, osteocytes, and chondrocytes (FIG. 5E-G). Culture of these cells in neuronal induction medium, similar to human cells, resulted in the formation of neurospheres, and morphological changes with increased Nestin expression associated with neuronal phenotypes (FIG. 5C, G-I).

Figure 6:
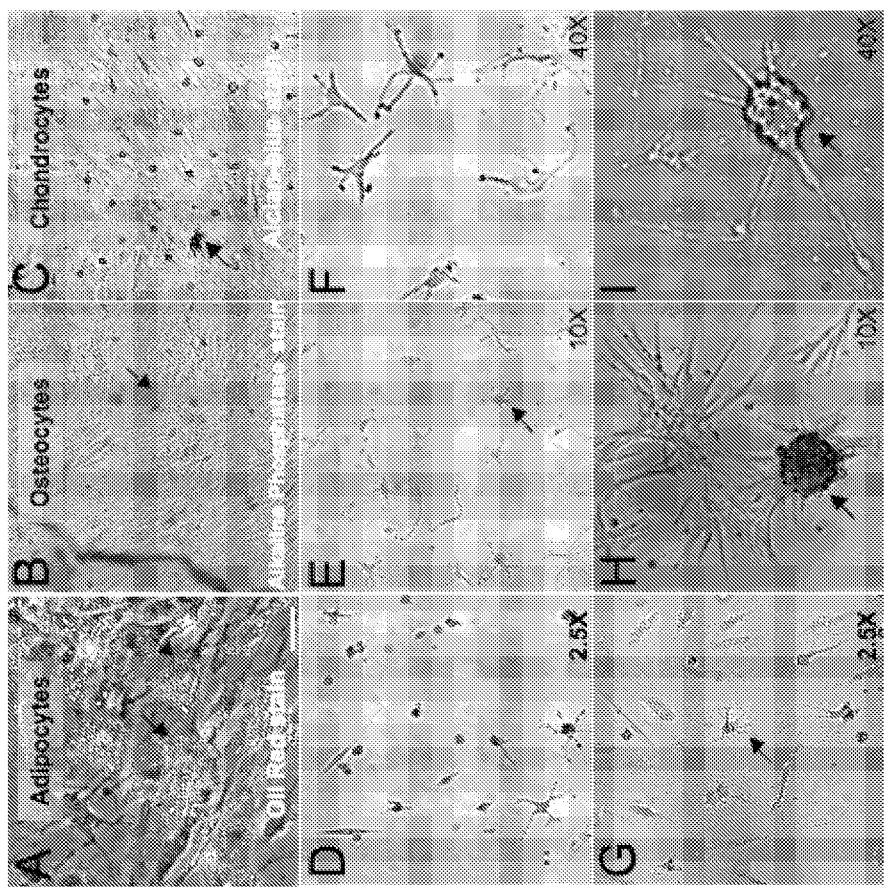
FIG. 6 illustrates human adherent BM cells isolated after 72 hours (ABMC) pluripotency showing trilineage transdifferentiation into adipocytes, osteocytes, and chondrocytes, as well as neurosphere induction, and neural differentiation. (A) Oil red staining of hABMC induced for adipocytes differentiation. (B) osteocyte differentiation with alkaline phosphatase staining. (C) Alcian-blue staining of hABMC induced for chondrocytes. (D-F) Neuronal induction of hABMC after 4 days showing neuronal morphology. (G-I) Induction of neural cells from neurosphere formation after one week.

We next evaluated the multilineage differentiation potential of ABMC from 10 human BM samples cultured in poly-L lysine coated flasks for 72 hours. Flow cytometric analyses at 72 hours revealed that human ABMC are >90% positive for, CD90, CD105, CD166, CD271, but had no expression of CD34, CD45, and CD14. Compared to traditional induction in 2-3 weeks, human ABMC were potently inducible to mesodermal trilineage differentiation into adipocytes, osteocytes, and chondrocytes (FIG. 6A-C) within one week. Neural induction 18 resulted in morphological changes consistent with neural differentiation (FIG. 6D-F), with typical oligodendroglial morphology in cells elaborating multiple primary dendrites (FIG. 6F), and with stronger potency compared to culture expanded cells from the same patient (FIG. 7I).

The numbers of neurospheres generated from ABMC (n=12 performed in 6-well plates in triplicates) were slightly higher but not significantly different than those neurospheres generated from the same patients' MSCs that were expanded in culture for 6-8 weeks. However, compared to culture expanded MSC, ABMC were more potently inducible to the spinal cord resident neural precursor tissues as demonstrated by upregulated immunoreactivity to the astrocytes precursor marker Nestin (FIG. 7C), the oligodendrocytes precursor marker, platelet derived growth factor receptor-alpha (PDGFR-α) (FIG. 7G), and the neuronal precursor marker, type III β-tubulin epitope J1 (TuJ1) (FIG. 7H).

Figure 7:
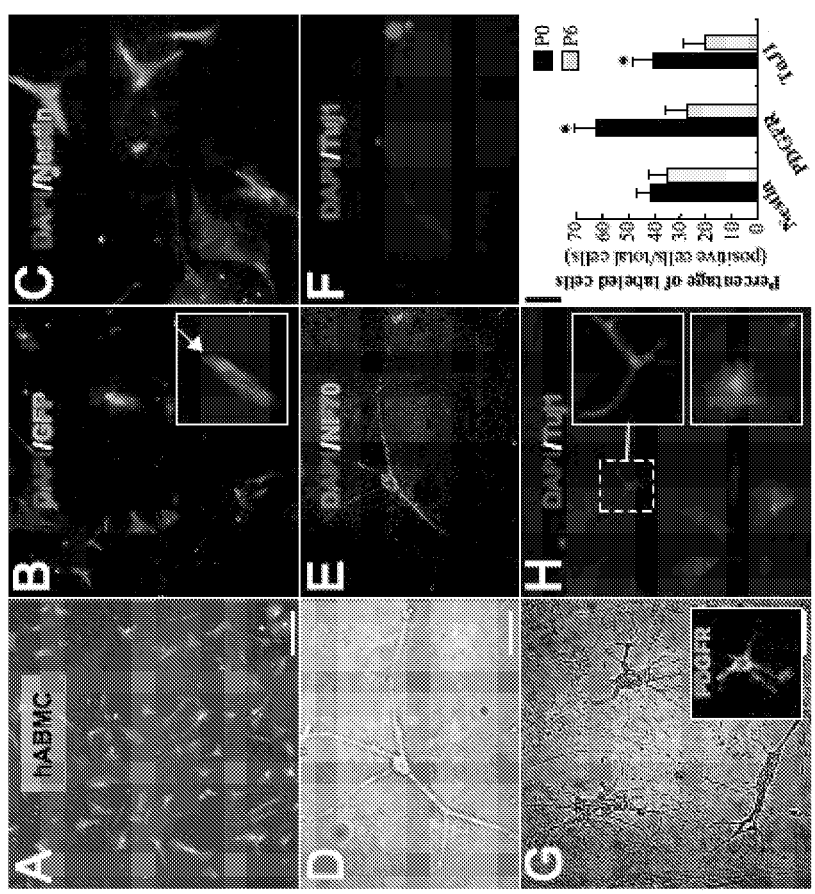
FIG. 7 illustrates human adherent BM cells isolated after 72 hours (ABMC) neural differentiation. (A) Bright field image of hABMC before induction. (B) hABMC transfected with GFP. (C) Expression of Nestin in hABMC. (D) Neuronal induction of hABMC after 4 days showing neuronal morphology. (E) Same neuron in D expresses NF70. (F) Same neuron in D expresses TuJ1. (G) Astrocytes-like morphology and PDGFR expression (inset) after neural induction. (H) Expression of TuJ1 in induced hABMC (upper inset shows higher magnification), while lower inert shows TuJ1 positive cell with long dendrites. (I) Percentage of Nestin, PDGFR, and TuJ1 cells in hABMC at passage 0 (P0) compared to cells from the same patient after passage 6. Scale bars in A, 20 mm, in D and G, 10 mm.
Figure 8:
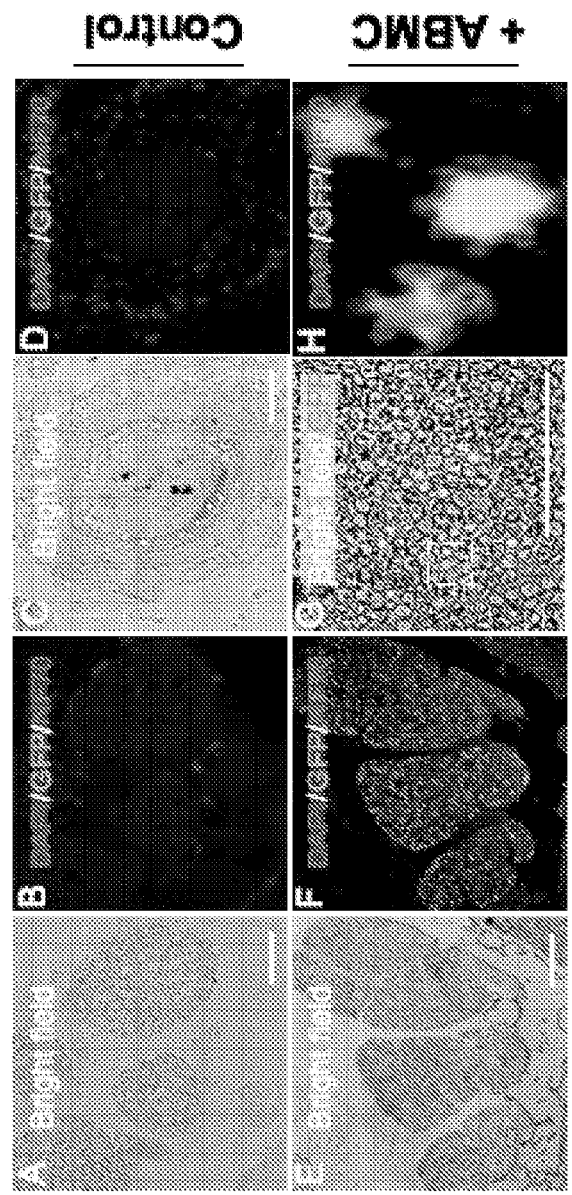
FIG. 8 illustrates immunofluorescence staining of corticospinal tract sections at 16 weeks in control and ABMC transplantation. (A-D) Sections of corticospinal tracts from of control dogs. (E-H) Section of corticospinal tracts from dogs treated with autologous ABMC. (A) Bright field section of lateral corticospinal tracts. (B) Fluorescent images of nuclear marker DAPI (blue), GFP (green), and NF70 (red) neuronal maker. No GFP expression was detected, while mild NF-70 expression was detected. (C) Bright field of ventral corticospinal tracts. (D) Fluorescent images of ventral corticospinal tracts in C stained with DAPI, GFP, and NF-70. (E) Lateral corticospinal tract from a control dog. (F) Fluorescent section of lateral corticospinal tracts showing colocalized GFP and NF-70. (G) Overlay of fluorescent images in F on the bright field in E. (H) Higher magnification of square in G showing GFP positive remyelinated axons with colocalized NF70 expression (yellow). Scale bars 100 µm.

Quantitative analyses of immunoreactive cells from the same patient (n=6 done in 6-well plates in triplicates) that were either induced for neural differentiation immediately, or after culture expansion revealed no significant difference in Nestin expression, while both PDGFRα and TuJ1 were significantly higher in ABMC than in culture-expanded MSCs (FIG. 7I). Therefore, these in vitro studies, though done in conditions that are not reflecting the in vivo behavior of the transplanted cells, demonstrate an advantage for using ABMC compared to culture expanded MSC.

Example 2

In Vivo Differentiation of ABMC in Canine Model

To establish a cell therapy strategy in a preclinical model, we transplanted autologous ABMC intrathecally in a canine model of severe SCI. Severe contusions to the dog spinal cord performed on 16 dogs similar to the established cat severe SCI model 24, resulted in sensory loss and hindlimb paralysis in all injured dogs (n=16) (FIG. 1H). One week after injury, animals were randomly divided into 4 groups (n=4/group), with group A serving as controls who received no cell treatment. Group B, C, and D dogs had BM aspirated from the iliac crest, and ABMC were isolated by adherence to plates for 72 hours. Cells were transfected with GFP expressing plasmid prepared as $2\times10^6$ ABMC/Kg in 150 μl of saline, and injected by lumbar puncture. Group B animals received unmanipulated ABMC. To investigate whether in vitro pre-differentiation of ABMC to neural lineage augment their in vivo neural potential, groups C and D animals received ABMC isolated at 72 hours that were induced for neural differentiation for either the last 24 hours (Group C), or for the full 72 hours (Group D).

Locomotor performance and functional recovery of hind limbs were evaluated every 4 weeks for 16 weeks after transplantation using a 15-point videotaping scoring system developed for canine SCI 25. Motor function of the hind limbs was intact in all animals before SCI, and they all scored 14-15 points (FIG. 1H). After injury, dogs were paraplegic with no deep pain sensation, and hind limb scores were zero. No significant differences (P=0.75) were measured between the three groups of dogs B, C, and D, receiving unmanipulated ABMC (n=4), or ABMC induced for neuronal differentiation for either 24 hours (n=4) or 72 hours (n=4). 7 Unlike control treated dogs in group A, dogs receiving autologous ABMC transplant (n=12) reached near maximum recovery at 8 weeks post transplant with significant recovery of their motor function at 16 weeks (FIG. 1H, and Table 1), and enhanced spontaneous hindlimb movements (FIG. 1I) detected within the first week, suggesting early local neuroprotective effects of ABMC. At 16 weeks after treatment, dogs were euthanized and spinal cords were fixed, and analyzed by histology and immunostaining. Sections from control dogs showed severe vacuole formation, in contrast to minimal cavitation in ABMC treated sections (FIG. 1A-C). Immuno-staining with anti-myelin basic protein (MBP) antibodies revealed significant remyelination in ABMC treated dogs compared to controls (FIG. 1D-G). MBP staining in ABMC sections reached up to 85% of MBP levels in intact cords (FIG. 1D-G), indicating substantial remyelination.

TABLE 1

Recovery of locomotor activity after ABMC injection post severe SCI in dogs
Open field score
(mean + s.e.m)

|  | Week 1 | Week 4 | Week 8 | Week 12 | Week 16 |
| --- | --- | --- | --- | --- | --- |
| Control (n = 4) | 1.9 + 0.1 | 2.2 + 1.2 | 3.6 + 2.1 | 3.8 + 0.6 | 3.5 + 0.8 |
| ABMC (n = 4) | 1.7 + 0.2 | 8 + 2.5 | 11 + 0.9 | 11 + 1.4 | 11 + 2.2 |
| ABMC + (24 h)(n = 4) | 1.8 + 0.3 | 8.9 + 2.1 | 10.9 + 0.8 | 12 + 1.2 | 11 + 1.9 |
| ABMC + (72 h)(n = 4) | 1.9 + 0.1 | 8.7 + 1.8 | 9.9 + 1.2 | 12 + 1 | 12 + 1.8 |

Figure 2:
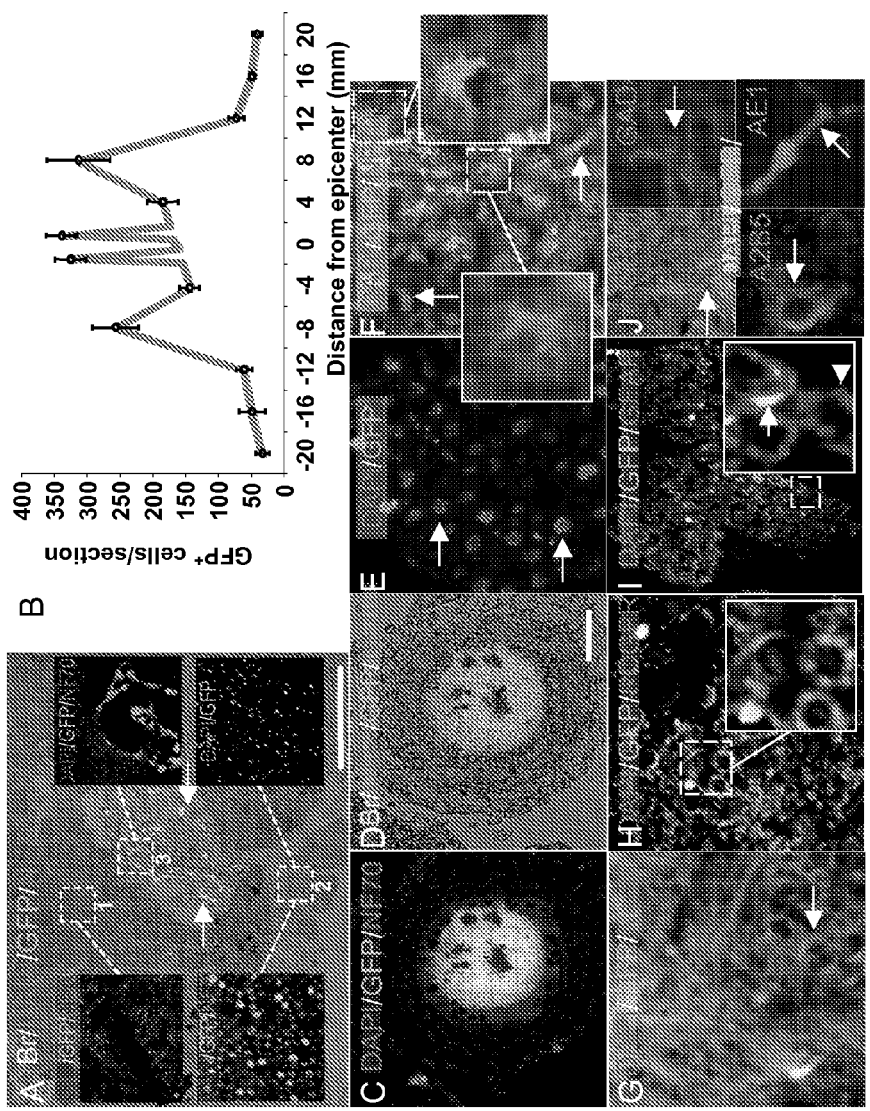
FIG. 2 illustrates multicolor immunofluorescence staining of SCI sections from dogs treated with autologous ABMC. (A) Cross section of spinal cord injury showing well organized tissue bridging the spinal cord gap (arrows) that was only observed in sections from dogs treated with autologous ABMC. Section is a low power overlay of bright images and fluorescent images of nuclear marker DAPI (blue), GFP (green) as a marker for transplanted ABMC, and NF70 (red) as a neuronal maker. GFP expression was widespread in both the gray and white matter, and surrounding nerve roots. Square area 1 in the gray matter of spinal cord showing colocalized GFP and NF70 staining. Square area 2 of cross-section in ventral corticospinal tracts showing higher magnification of GFP expression (right), and axons with GFP colocalized with NF70. Scale bar, 200 µm. (B) Distribution of GFP positive cells according to distance from epicenter. (C-F) Cross-sections of ventral corticospinal tracts demonstrating the immunoreactivity to GFP and NF70. (C) Ventral corticospinal tract showing colocalized GFP and NF70 and illustrating the substantial neuronal differentiation of GFP cell derivatives. (D) Overlay of the section in C on bright field. (E) Higher magnification showing GFP positive remyelinated axons with structural NF70 expression (inert). (F) Overlay of the section in E on bright field. (G) Colocalized GFP and Nestin staining. (H) Colocalized GFP and PDGFR staining, inset shows magnification of the square area. (I) Colocalized GFP and GFAP staining, inset shows magnification of the square area. Arrow in inert indicates GFP positive axon, while arrowhead points to an axon lacking GFP expression. (J) Colocalized GFP and GRM1, GAD, A2B5, and AE staining in areas of grey matter near the central canal. DAPI is used for nuclear staining in all sections. Scale bars in A, 200 µm, in D and F, 10 µm.
Figure 9:
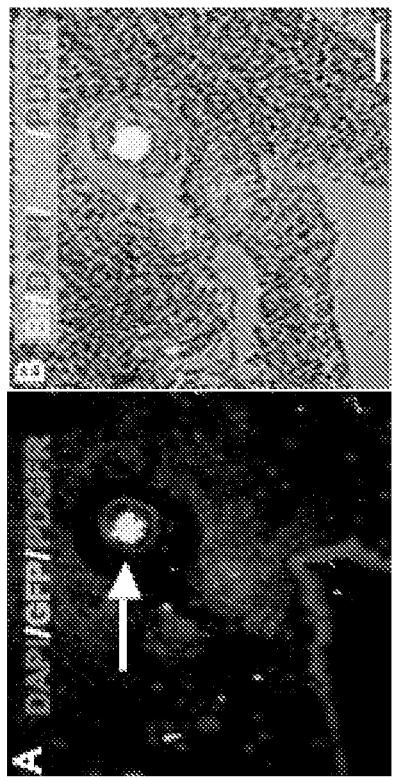
FIG. 9 illustrates BM-derived cells positive for GFP and PDGFR were surrounding the central canal and associated with small vessels within the spinal cord. (A) Fluorescent images of nuclear marker DAPI (blue), GFP (green) as a marker for transplanted canine ABMC, and PDGFR (red) maker. DAPI nuclei lines the central canal at the bottom left of the image. (B) Overlay of the fluorescent images on the bright field showing GFP positive axons and small spinal cord vessels. Scale bars, 50 µm.

To investigate the mechanisms of remyelination, and whether ABMC transplant enhances regeneration of injured axons, we performed multicolor immunohistochemistry using GFP as a marker for the transplanted ABMC in association with the spinal cord resident neural progenitor markers. GFP-positive cells were detected within the SCI lesion boundaries (FIG. 2A), but not in sections from control dogs (FIG. 8A-D). Numerous GFP positive cells were widely distributed from the epicenter (FIG. 2B), and were found in the gray and white matter of injured spinal cord, and distributed at the lesion boundary zone, around the central canal, and in the contralateral gray matter (FIG. 2A), indicating that the intrathecally injected BM cells migrated rostrally to the site of injury. BM-derived cells positive for GFP and PDGFR were found surrounding the central canal and associated with small vessels within the spinal cord (FIG. 9), which developed possibly through neovascularization. Additionally, at least 30% of GFP-positive cells in the gray matter were also positive for the 70 kDa neurofilament (NF70), a specific marker for mature neurons (FIG. 2A).

Figure 10:
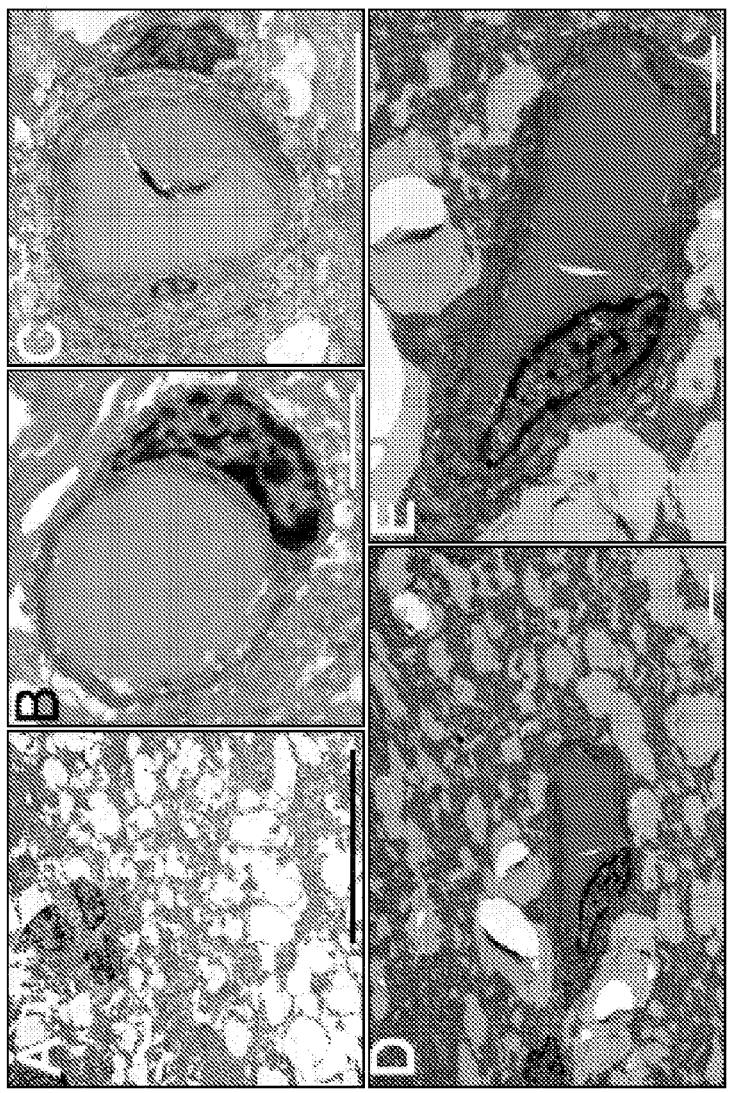
FIG. 10 illustrates electron microscopic imaging of sections of sections of SCI in control dogs demonstrating marked vacuolation, and minimal axonal sparing that reconstituted less than 1% of sections. (A) Marked vaculation and single spared axon in low power filed of SCI control dog. (B) Spared axon with normal myelination. (C) Myelin forming cell with glial scarring. (D) Excessive vaculation, and scarring surrounding myelin forming cell with no evidence for remyelination. (E) High power image of D. Scale bars, 1 µm.

The dorsal funiculus of the spinal cord consists largely of myelinated axons. Intense GFP staining was observed in the dorsal funiculus with several cells with large nuclear and cytoplasmic boundaries, indicating peripheral myelination. In sections from control animals, electron micrographs demonstrated demyelinated axons, extensive vacuolation, and glial scarring in an extracellular environment free of astrogliosis (FIG. 10). Quantitative analysis of central versus peripheral myelination in electron micrographs of sections from the ABMC transplanted dogs demonstrated that remyelinated axons are predominantly from peripheral-like myelin forming cells (FIG. 11A-C). Oligodendrocyte-myelinated axons with central myelination and characteristic thin myelin sheaths were observed in the smaller axons (FIG. 11D-F) in nearly one third of the total remyelinated axons.

Figure 11:
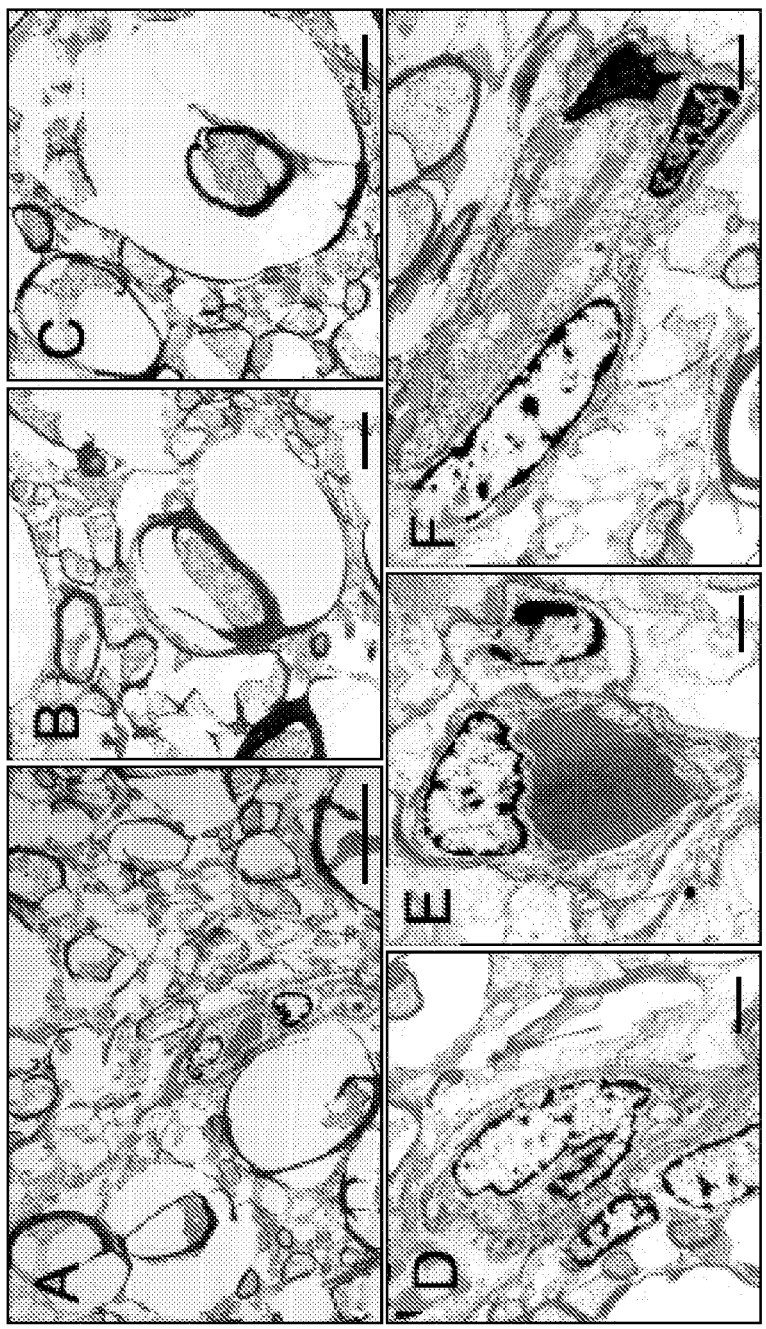
FIG. 11 illustrates electron microscopic imaging of sections of SCI dogs treated with ABMC demonstrating extensive axonal regeneration. (A) The regenerated axons were smaller in diameter, and multiple axons were associated with multinucleated myelin-forming cells suggesting lateral myelination. Limited vaculation and single spared axon in low power filed of SCI control dog. (B) Remyelinated axons with thick rim. (C) Multiple small axons surrounding a larger remyelinated axon. (D) Myelin forming cells engaging multiple axons. (E) Myelin forming cell with multilobular nuclei. (F) Large myelin forming cell with multiple nuclei and a surrounding basement membrane. Scale bars, 1 µm.

These remyelinated axons were found to be dually positive for GFP and GFAP (FIG. 2I), and were associated with astrocytes characterized by multilobular nucleoli and large intermediate-filament-rich processes that extended to multiple remyelinated axons (FIG. 11). Astrocytes and myelin-forming cells derived from GFP-labeled ABMC were also detected in the recovered spinal cord lesion. Moreover, we detected significantly more GFP positive axons expressing NF70 within cross sections of the ventral corticospinal tracts (FIG. 2C-F) in the ABMC treated dogs, with GFP expression clearly marking remyelinated axons (FIG. 8E-H, and inert in FIG. 2F), while none were detected in controls (FIG. 8A-D).

Regeneration of ventral and lateral corticospinal tracts, controlling voluntary movements, from GFP-positive ABMC suggests more robust axonal regeneration within the lesion site in the transplanted dogs and reveals the neural regeneration potency of ABMC, since these tracts were traditionally valued as the least capable of regeneration. Furthermore, the predominance of double-labeled profiles of GFP positive cell expressing neural progenitor markers matched the avid neural differentiation in the grey and white matter. GFP-positive cells expressed markers of the resident neural precursor tissues including the neural progenitor marker Nestin in a high-density synaptic appositions (FIG. 2G), the oligodendrocyte precursor marker PDGFR in a lower-density synaptic appositions (FIG. 2H), and the astrocyte precursor marker GFAP in nerve bundles (FIG. 2I).

GFP positive ABMC contributed to the terminal neural cell fate, as demonstrated by detection of GFP positive cells that colocalized as shown by immunoreactivity with excitatory, inhibitory (GABA) and cholinergic neurotransmitter markers. Cells dually labeled with GFP and either the excitatory metabotropic glutamate receptor-1 GRM1, the inhibitory glutamate decarboxylase (GAD) as a marker for GABAergic signals, and the cholinergic acetylcholinestrase (AE-1) signals were detected (FIG. 2J) in the regenerated cord. Additionally, we observed infrequent GFP positive cells that colocalized as shown by immunoreactivity with A2B5, a ganglioside antigen present in the common glial precursors O-2A (FIG. 2J) that have neural stem cell features. Collectively, these data demonstrate ABMC-derived neural regeneration within the spinal cord microenvironment.

Figure 12:
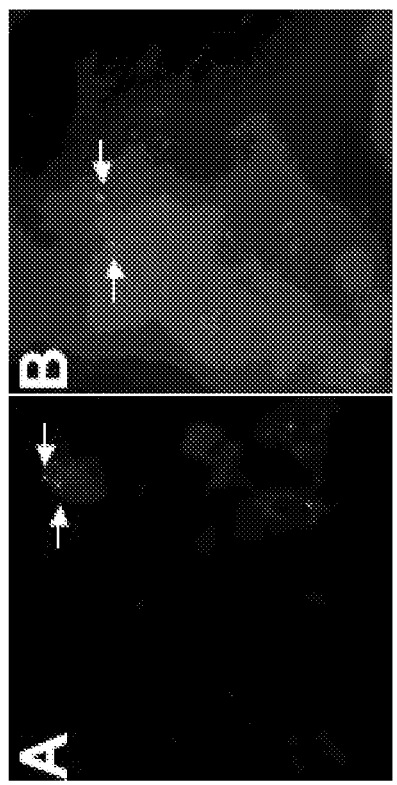
FIG. 12 illustrates FISH analysis of sections of MSC treated SCI in dogs demonstrating normal diploid cells (arrow) labeled with canine chromosome 35 probe with no evidence of fusion. (A) DAPI stained nucleus showing diploid ch.35 stained with red labeled probe (Arrows). (B) Higher magnification of the diploid nucleus stained with ch.35 red probe and in a GFP positive cell.

To exclude the possible occurrence of fusion events as a mechanism for regeneration, we analyzed sections of canine spinal cords that were subjected to grafting experiments. DAPI nuclear stained GFP expressing cells were examined using a canine chromosome 35 fluorescent in situ hybridization (FISH) probe. All examined cells (n=500) were diploid (FIG. 12).

Example 3

In Vivo Differentiation of ABMC in Humans

Preclinical studies in the severe SCI canine model revealed that the intrathecally transplanted autologous ABMC homed to the injury site, and resulted in spared white and gray matter, neuronal and axonal regeneration, neovascularization, astrocytes proliferation with significant remyelination, and functional improvement in locomotor scores, with no side effects detected.

Figure 3:
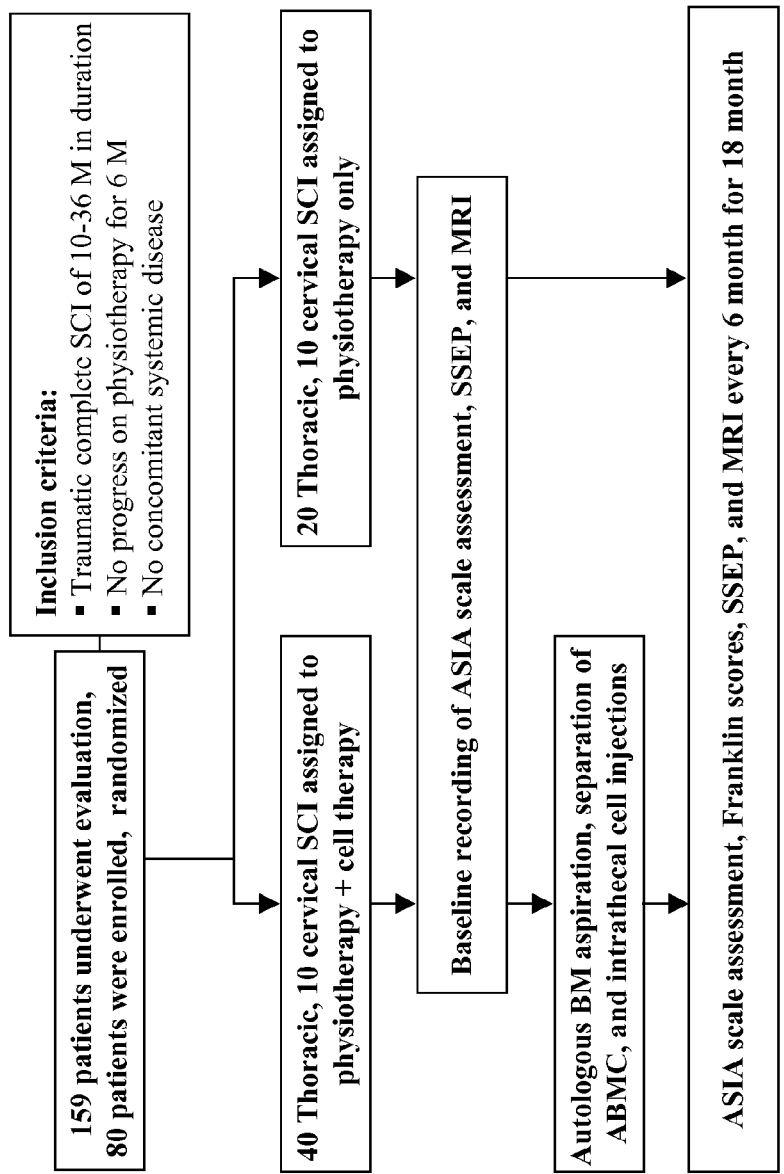
FIG. 3 illustrates study design of autologous intrathecal transplantation of ABMC in chronic complete spinal cord injury patients. Diagram shows enrollment, inclusion criteria, and follow up criteria.

These data led us to initiate a randomized phase I/II clinical trial to investigate the safety and efficacy of autologous intrathecal transplantation of ABMC in complete cervical and thoracic levels SCI patients. Selection criteria (FIG. 3) included patients who had completed at least 6 months of physiotherapy post injury with no spontaneous recovery. Patients studied were 9 females and 71 males, aged 16-45 years. The period since their injury ranged from 12-36 months with complete ASIA A traumatic SCI, neurological levels between C3 and T12, no evidence of neurological improvement for at least 6 months, and no concomitant systemic diseases (FIG. 3). During the enrollment period, 159 patients with complete chronic SCI were evaluated. A total of 80 patients were enrolled after signing an informed consent, under a protocol approved by Cairo University and Al-Azhar University clinical trial review committees.

Patients were randomized into two balanced groups: 50 patients; 40 thoracic and 10 cervical SCI were assigned to autologous ABMC transplant in combination with standard physiotherapy, while 30 matched patients, 20 thoracic and 10 cervical SCI were assigned to standard physiotherapy only, as a control group. Patients were assessed before cell therapy treatment to establish baseline measures. Both treated patients and the parallel control patients were monitored, and ASIA scale measurements were performed by blinded observers over the trial period, at the independent military forces center for physical medicine, rehabilitation and rheumatology. The risks associated with lumbar puncture and cell injections raised significant ethical concerns that limited the inclusion of a sham-injected control group.

Patients were assessed by clinical examinations for the development of neuropathic pain, cysts, syringomyelia or cell overgrowth. All transplant patients then received BM aspirates, from which autologous minimally manipulated BM cells were allowed to adhere for 72 hours (ABMC) under sterile conditions at the Stem Cells Unit of Cairo University hospital. Prior to transplantation of ABMC, samples were checked for cell phenotype, viability, and sterility. All 50 patients treated with autologous ABMC cell therapy by intrathecal transplantation through lumbar puncture received a cumulative target cell dose of $2 \times 10^6$ cells/kg, and the procedure was repeated monthly until this target dose was achieved (Median was 4 injections, range was 1-8 injections). ASIA and FIM score measurements and SSEP were examined, and MRI of the spinal cord were performed in all patients who consented to and tolerated MRI at baseline before transplantation and every six month for 18 months.

The trial data were regularly reviewed by the Egyptian Ministry of Health review committee, and by an independent German review committee. The 50 patients receiving cell therapy experienced mild side effects common with lumbar punctures including headache (30 patients; 60%), lower back pain (5 patients; 10%), involuntary movements (8 patients, 16%), and disturbance of vision (1 patient, 2%). All the aforementioned side effects were temporary and lasted from 12 hours to few days following lumbar puncture, and were completely resolved by symptomatic treatment. For up to 18 months post-transplantation, no long-term side effects were detected in ABMC treated patients, and none of the treated patients experienced infection, leakage of cerebrospinal fluid, additional neuropathic pain, spinal deformity, or developed any masses visible on MRI imaging.

Figure 4:
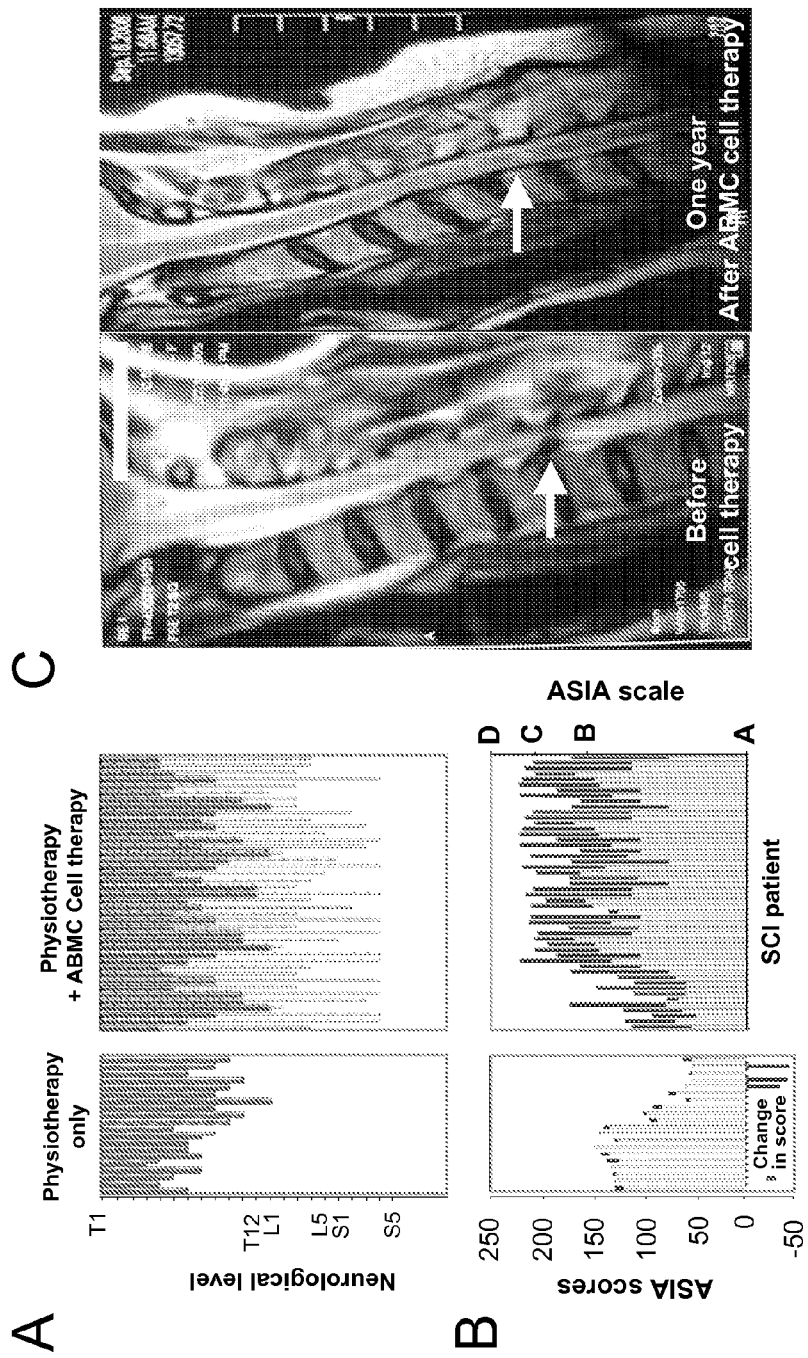
FIG. 4 illustrates recovery of chronic SCI patients measured at 18-month after transplantation of autologous ABMC. (A) Enhanced neurological levels in autologous ABMC treated patients compared to controls. Control patients retained a thoracic neurological level between thoracic 1 and 12 (T1-T12) levels, while patients treated with autologous ABMC gained lumbar and sacral neurological levels up to S5. (B) Changes in ASIA scores (left axis) and ASIA scales (right axis) in treated patients compared to controls. Three control patients had lower ASIA scores after 18 month than their base line scores, while patients treated with cell therapy showed improved scores. (C) MRI images before and 12-month after autologous ABMC transplantation (patient 6 with cervical SCI) showing compression and edema of the spinal cord at C6-C7 level, while the image one year after treatment demonstrated healed area with minimal gliosis.

All patients who received autologous ABMC therapy in addition to standard physio-therapy had a favorable response and significant improvement in their neurological functions compared to the control patients who received physiotherapy only (FIG. 4). Patients treated with autologous ABMC had a significant increase in their ASIA scores and FIM scores and recovery of electrophysiological muscle function at 6-months post transplant (FIG. 4A-B).

At 18 month post transplant (Table 2), 20 thoracic SCI patients (50%) showed an improved ASIA scale from grade A to grade C, 15 patients (37.5%) improved from grade A to grade B, while 5 patients (12.5%) remained in grade A (Detailed thoracic SCI patients criteria are listed in table 3). For the 10 cervical SCI patients treated with ABMC cell therapy, 2 patients (20%) improved from grade A to grade C, 3 patients improved from grade A to grade B, and 5 patients remained in grade A (Detailed cervical SCI patients criteria are listed in table 4). These changes were associated with recovery of spinal cord compression and edema (shown in FIG. 4C in MRI images from patient 6 with a C6-C7 cervical SCI at one-year post transplant). Moreover, these changes were associated with enhanced daily activities and significant improvement in quality of life. Two representative patients; patient 1 (with a C6 cervical SCI) was quadriplegic, and patient (with a T9 thoracic SCI) was hemiplegic before cell therapy, and both were able to walk and regain mobility nine month to one year after cell therapy.

Figure 13:
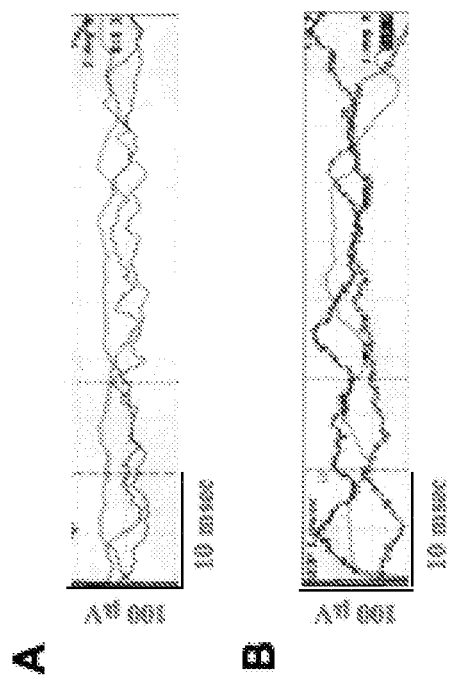
FIG. 13 illustrates motor Evoked Potential responses recorded in the posterior tibialis muscle in an ABMC treated patient and a control patient (representative recordings from one patient from each group). (A) Recordings from control patient with flat activity. (B) ABMC treated patient with recordings done one year after therapy. Recovery was evident in the ABMC treated patient by electrically evoked response with a latency of 20-30 msec recorded for the posterior tibialis muscle.

Regardless of scale measurements, all patients treated with autologous ABMC, including those who remained in ASIA grade A, noticed improved neurological functions as early as 4-6 weeks post transplant. Patients experienced enhanced response to tactile and sensory stimuli first, and later increased muscle strength that was noted first in the distal muscles of lower extremities and then in the thigh muscles. Patients with ASIA grade improvement showed better trunk movements that allowed them to sit and turn in bed. Additionally, improved muscle strength was associated enhanced sexual potency, and with stronger bowel and bladder sphincter controls that allowed these patient to live catheter-free. These effects were reflected in the improved neurological levels and FIM ABMC treated patients compared to controls (FIG. 4A, and Tables 3-4) All patients showed no cortical SSEP before therapy, while 65% of patients treated with ABMC but none of the control patients showed reappearance of cortical impulse (FIG. 13) at 6-month to one year post transplant. Thus autologous ABMC cell therapy significantly improved motor and sensory functions in chronic complete SCI patients.

TABLE 3

Thoracic SCI patient demographics, treatment and clinical outcome 18-month after therapy.

| Pt. # | Age/sex | SCI Level | BM inj. | Therapy | ASIA score Before/After | FIM score Before/After |
|---|---|---|---|---|---|---|
| 1 | 18/M | T4 | 5 | PT + ITC | 76/171 | 6/52 |
| 2 | 18/F | T6 | 3 | PT + ITC | 112/208 | 11/54 |
| 3 | 36/M | T8 | 3 | PT + ITC | 112/216 | 7/53 |
| 4 | 22/F | T12 | 1 | PT + ITC | 168/206 | 6/26 |
| 5 | 40/M | T10 | 3 | PT + ITC | 148/218 | 18/56 |
| 6 | 38/M | T10 | 5 | PT + ITC | 144/221 | 5/52 |
| 7 | 32/M | T5 | 6 | PT + ITC | 104/185 | 24/42 |
| 8 | 28/F | T8 | 6 | PT + ITC | 132/221 | 13/52 |
| 9 | 32/M | T5 | 5 | PT + ITC | 104/182 | 10/30 |
| 10 | 27/M | T4 | 4 | PT + ITC | 76/171 | 8/52 |
| 11 | 22/M | T6 | 5 | PT + ITC | 112/208 | 8/54 |
| 12 | 27/F | T8 | 3 | PT + ITC | 112/218 | 7/53 |
| 13 | 35/F | T12 | 8 | PT + ITC | 165/206 | 4/26 |
| 14 | 26/M | T10 | 8 | PT + ITC | 148/218 | 18/56 |
| 15 | 35/M | T10 | 3 | PT + ITC | 144/221 | 5/52 |
| 16 | 26/M | T5 | 4 | PT + ITC | 104/185 | 22/42 |
| 17 | 28/M | T8 | 6 | PT + ITC | 132/221 | 11/52 |
| 18 | 26/M | T5 | 2 | PT + ITC | 104/182 | 8/50 |
| 19 | 28/M | T7 | 5 | PT + ITC | 116/210 | 8/52 |
| 20 | 30/M | T6 | 4 | PT + ITC | 76/171 | 8/52 |
| 21 | 26/M | T11 | 6 | PT + ITC | 135/218 | 5/49 |
| 22 | 21/F | T11 | 2 | PT + ITC | 163/205 | 4/25 |
| 23 | 28/M | T7 | 8 | PT + ITC | 106/172 | 9/32 |
| 24 | 32/M | T5 | 8 | PT + ITC | 76/172 | 6/48 |
| 25 | 37/F | T8 | 4 | PT + ITC | 112/208 | 5/54 |
| 26 | 33/M | T9 | 4 | PT + ITC | 112/218 | 7/50 |
| 27 | 26/M | T12 | 1 | PT + ITC | 158/195 | 4/31 |
| 28 | 23/M | T7 | 3 | PT + ITC | 150/219 | 17/54 |
| 29 | 21/M | T10 | 5 | PT + ITC | 126/134 | 22/30 |
| 30 | 19/M | T5 | 4 | PT + ITC | 164/216 | 22/45 |
| 31 | 17/M | T8 | 5 | PT + ITC | 132/212 | 11/52 |
| 32 | 26/M | T7 | 5 | PT + ITC | 185/172 | 7/31 |
| 33 | 30/F | T8 | 3 | PT + ITC | 112/203 | 7/47 |
| 34 | 45/M | T12 | 2 | PT + ITC | 168/206 | 6/27 |
| 35 | 32/M | T19 | 3 | PT + ITC | 148/192 | 18/45 |
| 36 | 23/F | T4 | 5 | PT + ITC | 144/206 | 13/52 |
| 37 | 35/M | T6 | 5 | PT + ITC | 104/185 | 24/42 |
| 38 | 37/M | T8 | 5 | PT + ITC | 132/221 | 13/52 |
| 39 | 41/M | T5 | 5 | PT + ITC | 104/162 | 16/30 |
| 40 | 19/M | T4 | 4 | PT + ITC | 76/171 | 8/52 |
| 41 | 15/M | T6 | — | PT | 95/104 | 13/13 |
| 42 | 34/M | T7 | — | PT | 112/115 | 15/15 |
| 43 | 29/M | T5 | — | PT | 100/108 | 13/13 |
| 44 | 26/M | T9 | — | PT | 154/159 | 11/11 |
| 45 | 24/M | T19 | — | PT | 164/164 | 13/13 |
| 46 | 37/M | T8 | — | PT | 145/147 | 11/11 |
| 47 | 24/M | T12 | — | PT | 170/170 | 13/13 |

TABLE 2

Clinical response in all SCI patients at 18-month post treatment

| | Standard physiotherapy | | Standard Physiotherapy + ABMC | |
|---|---|---|---|---|
| Clinical response | Cervical SCI (n = 10) No. of patients (%) | Thoracic SCI (n = 20) No. of patients (%) | Cervical SCI (n = 10) No. of patients (%) | Thoracic SCI (n = 20) No. of patients (%) |
| COMPLETE | | | | |
| (ASIA scale A to E) | None in all groups | | | |
| PARTIAL | | | | |
| (ASIA scale A to D) | None in all groups | | | |
| (ASIA scale A to C) | None | None | 2(20) | 20(50) |
| (ASIA scale A to B) | 1(10) | 3(15) | 3(30) | 15(37.5) |
| NO RESPONSE | | | | |
| (ASIA scale A remains A) | 9(90) | 17(85) | 5(50) | 5(12.5) |

TABLE 3-continued

Thoracic SCI patient demographics, treatment and clinical outcome 18-month after therapy.

| Pt. # | Age/sex | SCI Level | BM inj. | Therapy | ASIA score Before/After | FIM score Before/After |
|---|---|---|---|---|---|---|
| 48 | 18/M | T8 | — | PT | 154/162 | 13/29 |
| 49 | 26/M | T9 | — | PT | 143/156 | 13/13 |
| 50 | 25/M | T10 | — | PT | 95/95 | 15/15 |
| 51 | 25/M | T8 | — | PT | 112/112 | 15/15 |
| 52 | 27/M | T8 | — | PT | 145/146 | 12/12 |
| 53 | 25/M | T9 | — | PT | 147/138 | 15/15 |
| 54 | 32/M | T8 | — | PT | 104/95 | 11/11 |
| 55 | 30/M | T6 | — | PT | 146/148 | 14/15 |
| 56 | 21/M | T8 | — | PT | 146/146 | 13/13 |
| 57 | 28/M | T5 | — | PT | 104/95 | 11/11 |
| 58 | 31/M | T9 | — | PT | 112/114 | 11/29 |
| 59 | 26/M | T10 | — | PT | 129/130 | 15/15 |
| 60 | 27/M | T8 | — | PT | 112/126 | 13/16 |

PT, physiotherapy, ITC, intrathecal ABMC cell therapy; Inj., number BM injections, FIM, functional independence measures

TABLE 4

Cervical SCI patient demographics, treatment and clinical outcome 18-month after therapy.

| Pt. # | Age/sex | SCI Level | BM injections | Therapy | ASIA score Before/After | FIM score Before/After |
|---|---|---|---|---|---|---|
| 1 | 18/M | C6 | 5 | PT + ITC | 70/126 | 1/14 |
| 2 | 26/M | C4 | 3 | PT + ITC | 59/100 | 3/14 |
| 3 | 34/M | C5 | 2 | PT + ITC | 61/144 | 2/21 |
| 4 | 19/M | C4 | 7 | PT + ITC | 60/110 | 4/12 |
| 5 | 29/M | C3 | 1 | PT + ITC | 67/78 | 1/5 |
| 6 | 37/M | C7 | 4 | PT + ITC | 79/171 | 1/18 |
| 7 | 24/M | C6 | 3 | PT + ITC | 63/120 | 4/21 |
| 8 | 18/M | C5 | 6 | PT + ITC | 50/92 | 3/20 |
| 9 | 16/M | C4 | 3 | PT + ITC | 70/118 | 4/14 |
| 10 | 25/M | C7 | 4 | PT + ITC | 54/111 | 2/15 |
| 11 | 18/M | C6 | — | PT | 62/68 | 1/1 |
| 12 | 36/M | C4 | — | PT | 59/25 | 3/3 |
| 13 | 25/M | C5 | — | PT | 61/64 | 2/2 |
| 14 | 28/M | C7 | — | PT | 60/27 | 1/1 |
| 15 | 26/M | C3 | — | PT | 67/40 | 1/1 |
| 16 | 28/M | C7 | — | PT | 79/87 | 2/2 |
| 17 | 30/M | C8 | — | PT | 63/67 | 2/2 |
| 18 | 25/M | C8 | — | PT | 95/104 | 4/4 |
| 19 | 33/M | C6 | — | PT | 70/126 | 3/4 |
| 20 | 23/M | C6 | — | PT | 59/109 | 2/4 |

PT, physiotherapy, ITC intrathecal ABMC cell therapy; FIM functional independence measure.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

I claim:

1. A method for treating a degenerative or traumatic injury to a nerve tissue or the brain in a vertebrate comprising:
   (a) isolating adherent bone marrow stem cells in the absence of cell passaging by:
      culturing a biological sample comprising adult bone marrow stem cells on a poly-L-lysine coated substrate for 2 to 72 hours, so that a layer of bone marrow stem cells adheres to said substrate; and washing any non-adherent cells from said substrate and collecting said adherent bone marrow stem cells;
   (b) suspending the adherent bone marrow stem cells in a pharmaceutically acceptable liquid to provide a bone marrow stem cell suspension; and
   (c) administering near said injury site said bone marrow stem cell suspension in an amount effective to elicit axonal regeneration or remyelination at the site of said injury.

2. The method of claim 1, wherein said suspension is administered by intrathecal injection through lumbar puncture into the cerebrospinal fluid adjacent said injury site.

3. The method of claim 1, wherein between about $10^4$ and about $10^7$ bone marrow stem cells/kg are cumulatively administered.

4. The method of claim 1, wherein the cumulative dosage of said bone marrow stem cells is administered periodically over a series of two or more injections.

5. The method of claim 4, wherein the periodic injections are performed monthly.

6. The method of claim 1, wherein said bone marrow stem cells comprise cells positive for one or more markers selected from the group consisting of CD44, CD73, CD90, CD105, CD166 and CD271.

7. The method of claim 1 wherein said bone marrow stem cells consist essentially of cells negative for the markers CD34, CD38 and CD45.

8. The method of claim 1, wherein said bone marrow stem cells elicit differentiation, post-administration, of a cell type selected from the group consisting of a myelin forming cell, an astrocyte precursor cell, an astrocyte, a neural progenitor cell, an oligodendrocyte precursor cell, an oligodendrocyte cell, a myelinated axon, and a mature neuron.

9. The method of claim 8, wherein said bone marrow stem cells elicit differentiation, post-administration, of a cell type positive for NF-70.

* * * * *